United States Patent [19]
Vargeese et al.

[11] Patent Number: 6,020,206
[45] Date of Patent: Feb. 1, 2000

[54] HOMOCYSTEINE ASSAY

[75] Inventors: Chandra Vargeese, Thornton; Sumedha Jayasena; Nebojsa Janjic, both of Boulder, all of Colo.

[73] Assignee: NeXstar Pharmaceuticals, Inc., Boulder, Colo.

[21] Appl. No.: 09/099,588

[22] Filed: Jun. 18, 1998

Related U.S. Application Data

[60] Provisional application No. 60/050,483, Jun. 23, 1997.

[51] Int. Cl.[7] .................................................. G01N 33/68
[52] U.S. Cl. ............................................... 436/89; 422/61
[58] Field of Search ............................. 436/89, 119, 164, 436/172; 422/61

[56] References Cited

U.S. PATENT DOCUMENTS

| | | | |
|---|---|---|---|
| 4,571,430 | 2/1986 | Bryne et al. | 560/148 |
| 4,940,658 | 7/1990 | Allen et al. | 435/4 |
| 5,274,122 | 12/1993 | Tolman et al. | 549/6 |
| 5,346,599 | 9/1994 | Stamler et al. | 204/180.1 |
| 5,438,017 | 8/1995 | Allen et al. | 436/89 |
| 5,478,729 | 12/1995 | Van Atta et al. | 234/456 |
| 5,559,038 | 9/1996 | Kolhouse et al. | 436/86 |
| 5,631,127 | 5/1997 | Sundrehagen | 435/4 |
| 5,668,173 | 9/1997 | Garrow | 514/557 |

FOREIGN PATENT DOCUMENTS

| | | |
|---|---|---|
| 0 269 352 B1 | 6/1988 | European Pat. Off. |
| 0 486 118 A1 | 5/1992 | European Pat. Off. |
| 0 618 312 A1 | 10/1994 | European Pat. Off. |
| 0 623 174 B1 | 11/1994 | European Pat. Off. |
| 0 726 322 A1 | 8/1996 | European Pat. Off. |
| WO 93/01496 | 1/1993 | WIPO |
| WO 93/15220 | 8/1993 | WIPO |
| WO 95/30151 | 11/1995 | WIPO |

OTHER PUBLICATIONS

Andersson et al. (1992) European Journal of Clinical Investigation 22:79–87 month unknown.
Andersson et al. (1993) Clin. Chem. 39:1590–1597 month unknown.
Araki and Sako (1987) Journal of Chromatography 422:43–52 month unknown.
Fahey et al. (1981) Analytical Biochemistry 111:357–365 month unknown.
Fiskerstrand et al. (1993) Clin. Chem. 39:263–271 month unknown.
Graham et al. (1997) JAMA 277:1775–1781 month unknown.
Jacobsen et al. (1989) Analytical Biochemistry 178:208–214 month unknown.
Kang et al. (1982) Pediatr. Res. 16:370–372 month unknown.
Mansoor et al. (1992) Analytical Biochemistry 200:218–229 month unknown.
Racker (1955) J. Biol. Chem. 217:867–875 month unknown.
Refsum et al. (1985) Clin. Chem. 31:624–628 month unknown.

(List continued on next page.)

*Primary Examiner*—Jill Warden
*Assistant Examiner*—Alex Noguerda
*Attorney, Agent, or Firm*—Swanson & Bratschun LLC

[57] ABSTRACT

This invention pertains to methods of determining the presence and/or quantity of homocysteine in a sample containing other thiol-containing compounds. The methods of this invention involve modifying the homocysteine to facilitate the separation of homocysteine from cysteine. An assay protocol comprises adjusting the conditions of the sample suspected of containing homocysteine so that homocysteine forms homocysteine thiolactone, separating the homocysteine thiolactone from free thiol-containing compounds present in the sample, including cysteine, reconverting the homocysteine thiolactone to homocysteine, and determining the presence and/or quantity of homocysteine in the sample by conventional means.

61 Claims, 20 Drawing Sheets

OTHER PUBLICATIONS

Refsum et al. (1989) Clin. Chem. 35:1921–1927 month unknown.

Stabler et al. (1987) Analytical Biochemistry 162:185–196 month unknown.

Stern et al. (1982) Journal of Biochemical and Biophysical Methods 7:83–89 month unknown.

Ueland et al. (1993) Clin. Chem. 39:1764–1779 month unknown.

Velury and Howell (1988) Journal of Chromatography 424:141–146 month unknown.

HOMOCYSTEINE ASSAY

This application claims the benefit of U.S. Provisional Application No. 60/050,483, filed Jun. 23, 1997.

FIELD OF INVENTION

The invention is directed to methods of determining the presence and/or quantity of homocysteine in a sample that contains other thiol-containing compounds. The methods of this invention involve modifying the homocysteine to facilitate the separation of homocysteine from other thiol-containing compounds. An assay protocol comprises adjusting the conditions of the sample suspected of containing homocysteine so that homocysteine forms homocysteine thiolactone, reacting free thiol-containing compounds present in the sample, including cysteine, with a thiol-capturing agent, reconverting the homocysteine thiolactone to homocysteine, and determining the presence and/or quantity of homocysteine present in the sample by conventional means.

BACKGROUND OF THE INVENTION

Homocysteine (Hcy), a thiol-containing amino acid, is a metabolic intermediate of both methionine (Met) and cysteine (Cys) production. The exclusive source of Hcy in mammals is a three-step conversion of the essential dietary amino acid Met in the "active methyl cycle". (Scheme 1).

Hcy may be removed from the active methyl cycle to combine with serine to form Cys via a cystathionine intermediate, a reaction which is catalyzed by cystathionine synthase (CS). Alternatively, Hcy may participate in the active methyl cycle by being methylated to Met, a reaction which is catalyzed by methionine synthase (5-methyltetrahydrofolate-homocysteine methyltransferase). The major metabolic pathway for the methylation of Hcy to Met is dependent on the cofactor activity of folate and vitamin $B_{12}$. Not surprisingly, elevated levels of serum Hcy have been associated with insufficient intake of vitamin $B_{12}$ or folate, or a deficiency in the ability to properly utilize these vitamins.

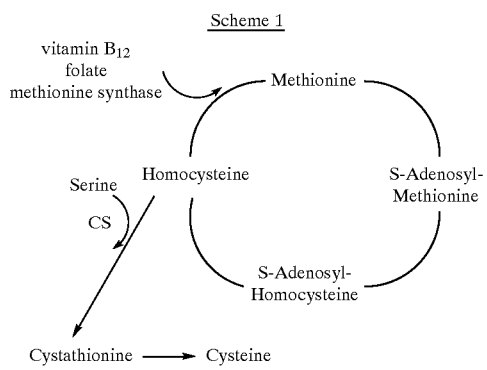

Scheme 1

Decreased levels of folate and Vitamin $B_{12}$, and thus a significantly higher Hcy concentration, have been observed in the amniotic fluid of pregnancies where the fetus was affected with a neural tube defect. Moderately elevated levels of Hcy usually can be brought into balance by administering folate, a treatment for which there are few adverse side-effects.

Elevated levels of Hcy are present in the serum and urine of patients with cystathionine synthetase deficiency who cannot convert Hcy to cystathionine, and in the serum and urine of patients with defects involving methionine synthetase who cannot convert Hcy to Met (Mudd, S H, in *The Metabolic Basis of Inherited Disease* (Senver, C G, ed.) McGraw Hill, N.Y., pp.693–734 (6th ed. 1989)). These genetic predispositions are the most common causes of homocysteinuria (build-up of Hcy in urine) in otherwise healthy patients. The clinical features of this disease are early, life threatening thromboembolism, mental retardation, and other tissue abnormalities.

Hcy in high concentrations is generally considered to be atherogenic and thrombogenic. In the last decade, over twenty case-controlled studies have consistently shown that plasma Hcy concentration is very frequently increased in patients with vascular disease (Ueland et al., in *Atherosclerotic Cardiovascular Disease, Hemostasis and Endothelial Function* (Francis, R B. Jr., ed.) NY, pp.183–236 (1992)). An excellent overview of the causes of homocysteinuria as well as an update on the current methods of clinical analysis can be found in Ueland et al. (1993) Clin. Chem. 39:1764–1779. A study by Graham et al. (1997) JAMA 277:1775–1781, confirms that an elevated plasma total Hcy level is established as a strong and independent factor associated with all categories of atherosclerotic disease in both men and women.

Thus, plasma and serum Hcy are established as indicators of several common disease states. Therefore, the clinical importance of Hcy has lead to an increased interest in developing an accurate assay for measuring Hcy in biological fluids.

Hcy exists in human plasma as various mixed disulfides. Normally, a major fraction of Hcy (approximately 70%) is protein bound via a disulfide bond to circulating proteins such as albumin. The remaining "free" Hcy (approximately 30%) is in the form of Hcy (reduced) or as mixed disulfides with other thiols such as Cys. The sum of these Hcy species present in plasma (protein-bound, free-disulfide and free-reduced) is referred to as the "total Hcy." Measurement of total Hcy in biological fluids preferably involves a pretreatment step to form the free reduced-form Hcy. However, measurement of free Hcy may be done without pretreatment, if desired. There are several techniques to quantitate total homocysteine (Hcy) as well as distinguish between the free (reduced and disulfide) and protein-bound (primarily albumin) forms.

The detection and/or separation of Hcy in biological samples by current methods is difficult due to the presence of multiple sulfhydryl species present in the sample. During the last two decades, assays for Hcy and Cys have mainly involved high performance liquid chromatographic (HPLC) methods. This analytical method discriminates between Hcy and Cys by differential adsorption and elution of the compounds on a chromatographic support. Many of these methods involve pre- or postcolumn derivatization of plasma sulfhydryls, for example, with ninhydrin (Clarke et al. (1991) N. Engl. J. Med. 324:1149–1155; Kang et al. (1986) J. Clin. Invest. 77:1482–1486; Andersson et al. (1992) Eur. J. Clin. Invest. 22:79–87), monobromobimane (Fiskerstrand et al. (1993) Clin. Chem. 39:263–271; Mansoor et al. (1992) Anal. Biochem. 200:218–229; Fahey et al. (1981) Anal. Biochem. 111:357–365; Velury and Howell (1988) J. Chromatography 424:141–146; Jacobsen et al. (1989) Anal. Biochem. 178:208–214; Refsum et al. (1989) Clin. Chem. 35:1921–1927), adenosine (Refsum et al. (1985) Clin. Chem. 31:624–628), N-methyl-N-(tert-butyldimethylsilyl) trifluoroacetamide (Stabler et al. (1987) Anal. Biochem. 162:185–196), halogenated sulfonyl benzofurazans (Araki and Sako (1987) J. Chromatography 422:43–52; Ubbink et al. (1991) J. Chromatography 565:441–446; Vester et al. (1991) Eur. J. Clin. Chem. Clin. Biochem. 29:549–554), o-phthaldialdehyde (Fermo et al. (1992) J. Chromatography 593:171–176), 4,4'-dithiodipyridine (Andersson et al. (1993) Clin. Chem. 39:1590–1597), 5,5'-dithiobis(2-nitrobenzoic acid) (Kuwata et al. (1982) Anal. Chem. 54:1082–1087; Reeve et al. (1980) J. Chromatography 194:424–428; Konouro et al. (1985) J. Chromatography 338:209–212; Studebaker et al. (1978) Anal. Chem. 50:1500–1503), or with electrochemical detection (Swift et al. (1986) Nutr. Reports, Int. 34:1–4; Manilow et al. (1989) Circulation 79:1180–1188; Smolin et al. (1982) J. Nutr. 112:1264–1272). Some of these methods, namely, electrochemical (Manilow) or derivatization with ninhydrin (Clark, Andersson, Kang), monobromobimane (Refsum) or N-methyl-N-(tert-butyldimethylsilyl)trifluoroacetamide (Stabler) have been used to measure Hcy in larger amounts of biological samples. Only monobromobimane (Mansoor) and halogenated sulfonyl benzofurazans (Araki) were able to detect other sulfhydryls in plasma. Recently (Mansoor, Andersson) methods have been described that measured total, free (non-protein-bound) and reduced Hcy in plasma.

In an example of Hcy analysis by HPLC which requires prior derivatization with fluorescent labels, such as bromobimane, the bromomethyl group reacts with the free thiol of Hcy, thus forming a thioether. A problem with this method, however, is that the bromobimane reagent also reacts with all other free thiols in solution. Therefore, chromatographic separation of the various derivatized sulfur-containing species is necessary. Thus, chromatographic methods have the disadvantages of being slow, labor intensive and expensive.

An enzymatic method for a Hcy assay is described by Sundrehagen et al., WO93/15220, where Hcy is assayed indirectly by measuring the product concentration following the enzyme catalyzed conversion of Hcy to S-adenosyl homocysteine.

Methods of analyzing sulfhydryl amino acids by gas chromatograph-mass spectrometer (GC-MS) means are known. Allen et al. (U.S. Pat. No. 4,940,658), describe analysis of, for example, Hcy by GC-MS using labeled Hcy as an internal reference standard.

Van Atta et al. (U.S. Pat. No. 5,478,729), describe a method of detecting Hcy in the presence of Cys comprising chemically modifying Hcy and Cys and then immunochemically detecting the modified Hcy by means of an antibody which specifically binds to the modified Hcy but not to the modified Cys.

Stern et al. (J. Biochem. and Biophys. Methods 7:83–88 (1982)) describe a method of purifying Met-free [$^{35}$S]Hcy thiolactone following its synthesis. In this method, [$^{35}$S]Hcy thiolactone is synthesized by treating [$^{35}$S]Met under harsh conditions (refluxing the Met in hypophosphorous acid and hydriodic acid for 22 hours), followed by chromatographic purification of the Hcy thiolactone on an alumina column. Met and any unreacted Hcy are retained by the alumina through its carboxyl group and are not eluted. The yield of the Hcy thiolactone by this procedure was only 5–10%.

A method for converting Hcy to Hcy thiolactone and an assay for determining this conversion spectrophotometrically at 240 nm was described by Racker (J. Biol. Chem. 217:867–874 (1955)). However, it was not recognized by Racker that this method could be used to selectively separate the thiolactone from free thiol-containing compounds. Furthermore, as evidenced by the cumbersome chromatographic methods currently used to assay for Hcy, the conversion of Hcy to Hcy thiolactone has clearly not been recognized as a useful tool for incorporation in a Hcy assay.

A need exists for an improved assay for Hcy which is simple, specific, quick to perform, readily adapted for use in clinical laboratories, and which avoids the need for costly and time consuming chromatographic separation.

SUMMARY OF THE INVENTION

The present invention pertains to methods for detecting Hcy in a sample that may contain Hcy, comprising the steps of (a) converting Hcy in the sample to Hcy thiolactone; (b) reacting free thiol-containing compounds in the sample with a thiol-capturing agent; (c) reconverting Hcy thiolactone to Hcy; and (d) detecting for the presence of Hcy in the sample. In one embodiment, the thiol-capturing agent is bound to a solid support. In this embodiment, the free thiol-containing compounds are reacted with the thiol-capturing agent, and the products of this reaction are removed from the sample. In another embodiment, the method for detecting Hcy is a homogeneous method and any unreacted thiol-capturing reagent in step (b) is quenched with a quenching reagent prior to step (c). In this embodiment, it is not necessary to remove the products of the reaction between the thiol-containing compounds and the thiol-capturing reagent from the sample.

Another embodiment of this invention pertains to a method for detecting the presence of Hcy in a sample that may contain Hcy wherein at least a portion of Hcy is in the disulfide form (protein-bound and free-disulfide). In this embodiment, the disulfide forms of all thiols in the sample, including Hcy, are first converted to free thiol compounds.

The present invention also pertains to methods for determining the quantity of Hcy in a sample that may contain Hcy, comprising the steps of (a) converting Hcy in the sample to Hcy thiolactone, (b) reacting free thiol-containing compounds in the sample with a thiol-capturing agent; (c) reconverting Hcy thiolactone to Hcy; and (d) determining the quantity of Hcy in the sample.

The present invention also provides a method for determining the presence and/or quantity of Hcy in a sample that may contain Hcy, comprising the steps of (a) converting Hcy in the sample to Hcy thiolactone; (b) reacting free thiol-containing compounds in the sample with a thiol-capturing agent; (c) reacting the Hcy thiolactone with a nucleophile; and (d) detecting the presence of the Hcy in the sample.

This invention also includes a kit for detecting Hcy in a sample, comprising: means for converting Hcy in a sample to Hcy thiolactone, a thiol-capturing agent, means for reconverting Hcy thiolactone to Hcy, and means for the detection and/or quantitation of Hcy. The kit may also comprise a releasing agent for liberating Hcy and other sulfur compounds from serum proteins and for reducing their disulfide forms.

The present invention also pertains to methods of detecting Hcy in a sample that may contain Hcy, comprising the steps of (a) converting Hcy in a sample to Hcy thiolactone; (b) reacting free thiol-containing compounds with a thiol-capturing agent; and (c) detecting the presence of Hcy thiolactone in the sample. In another embodiment, the disulfide forms of thiols in the sample are first converted to free thiol compounds.

DETAILED DESCRIPTION OF THE INVENTION

Figure 1:
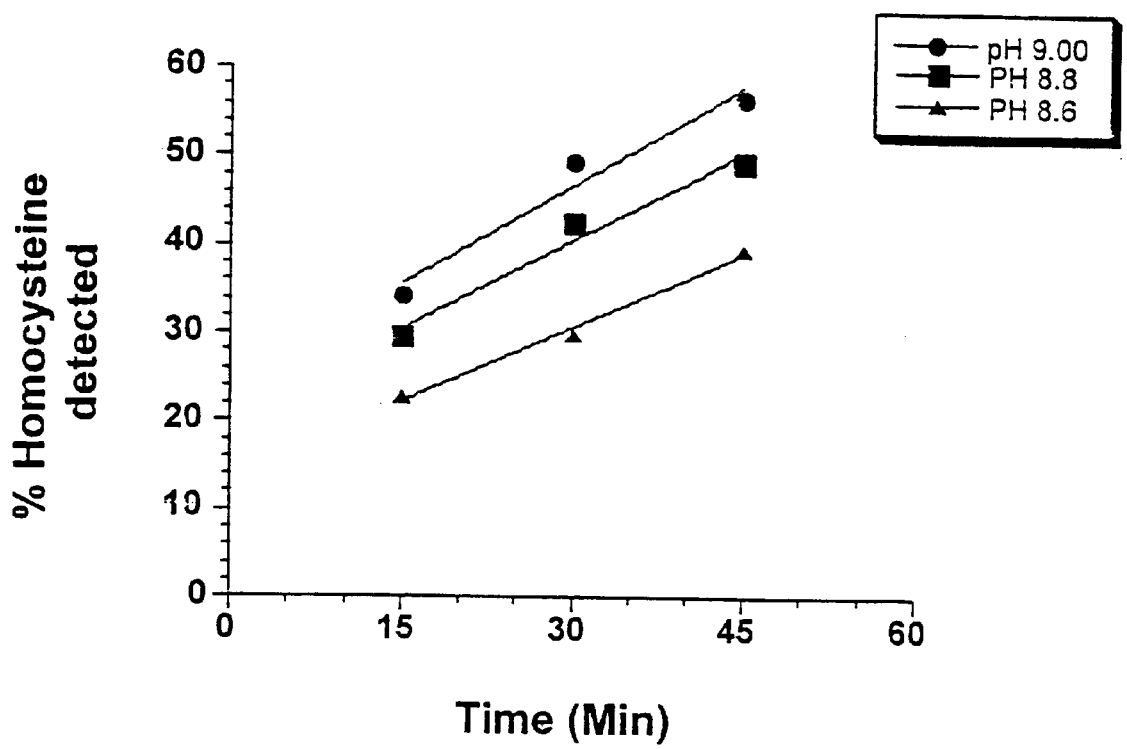
FIG. 1 depicts the percent Hcy detected in a sample at various time points and at different pH's. The triangles indicate a pH of 8.6, the squares indicate a pH of 8.8 and the circles indicate a pH of 9.0.

In the method of the present invention, the Hcy present in a sample is converted to Hcy thiolactone, in which the thiol group of Hcy is temporarily and reversibly protected. The remaining free thiol-containing compounds in the sample are readily reacted with a thiol-capturing agent which reacts with free thiol groups to allow separation of the Hcy thiolactone from other thiol containing compounds or to eliminate thiol-containing compounds in the sample. The conditions of the remaining sample containing the Hcy thiolactone are then adjusted so that the Hcy thiolactone is reconverted to Hcy, and any of a number of methods can be employed to rapidly detect and/or quantitate the Hcy present in the sample.

This invention pertains to methods for detecting an analyte in the presence of a homolog that is chemically related to the analyte. The methods of the invention further comprise separating an analyte in a sample, wherein the analyte has a specific functional group, from other compounds in the sample having the same functional group as the analyte.

The methods of this invention involve reversibly modifying the analyte under conditions wherein the homolog and primarily all other species in the sample are not modified to facilitate the separation of the analyte from the homolog. An assay protocol comprises reversibly modifying the analyte, separating the modified analyte from the homolog and other species in the sample, reconverting the modified analyte to the analyte form, and detecting the analyte. The term "homolog" as defined herein describes a compound in a series of organic compounds that have the same chemical functional groups, and which differ from one another by minor chemical variations, such as by an insertion of a —$CH_2$— group in the molecule. Examples of homologs within the scope of this invention include, but are not limited to, homocysteine and cysteine.

Hcy and Cys are homologs having the following structures:

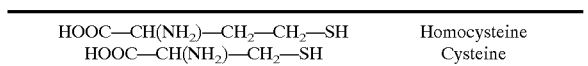

| HOOC—CH($NH_2$)—$CH_2$—$CH_2$—SH | Homocysteine |
| HOOC—CH($NH_2$)—$CH_2$—SH | Cysteine |

It is often difficult to separate these two homologs by traditional methods in order to accurately determine the presence and/or quantity of Hcy in a sample. The inventors of the present invention recognized that Hcy and Cys are chemically distinct and realized that this distinction could be exploited to design a fast and accurate Hcy assay. Hcy, which has a thiol group on the γ-carbon, can readily undergo an intramolecular cyclization to form a 5-membered γ-thiolactone ring. The equilibrium between the linear Hcy form and the cyclic Hcy thiolactone form in a sample can be manipulated by adjusting the pH of the sample. For example, below a pH of 5, greater than 99% of Hcy is in the form of Hcy thiolactone, and above pH 9, essentially all Hcy is in the ring-opened free thiol form. It is recognized that this equilibrium between the linear and cyclic forms of Hcy exists, and that there may be situations where the conversion of Hcy to Hcy thiolactone is incomplete. In the methods of the present invention, it is not necessary that all of the Hcy be converted to Hcy thiolactone in order to detect the presence of Hcy in a sample. In a preferred embodiment, essentially all of the Hcy is converted to Hcy thiolactone.

Cys has a thiol group on the β-carbon. The intramolecular cyclization of Cys to a β-thiolactone is extremely unfavorable thermodynamically, since the resulting 4-membered ring is highly strained. Therefore, under the conditions used in the methods of the present invention, essentially all of the Cys which may be present in the sample exists in the open free thiol form. Glutathione is a tripeptide found in all types of organisms and is an example of a naturally occurring substance having a thiol group and a carboxyl group which could form a 7-membered thiolactone ring. However formation of this thiolactone ring is also thermodynamically unfavorable.

Thus it is believed that Hcy is the predominant thiol-containing compound which will undergo ring formation under the conditions used in the present invention, and that other potential thiolactone-forming species will not interfere in the assay of Hcy in the methods of the present invention.

Before proceeding further with the description of the specific embodiments of the present invention, a number of terms will be defined.

The term "Hcy" as used herein refers to the open reduced thiol form of homocysteine.

The term "Hcy thiolactone" refers the γ-ring form of homocysteine.

The term "derivatized Hcy" as used herein refers to the open reduced thiol form of homocysteine produced by the reaction of Hcy thiolactone and a nucleophile.

The term "sample" as used herein is defined as anything which may contain Hcy for which an assay is desired. The sample may be a biological sample, such as a biological fluid from a host, for example, urine, blood, plasma, serum, saliva, semen, stool, sputum, cerebral spinal fluid, tears, mucus, amniotic fluid or the like. The biological sample may also be a biological tissue. Biological tissue refers to an aggregate of cells, usually of a particular kind together with their intercellular substance that form one of the structural materials of a human, animal, plant, bacterial, fungal or viral structure, including connective tissue, epithelium, muscle tissue, and nerve tissues. Examples of biological tissues include organs, tumors, lymph nodes, arteries and individual cells.

The term "analyte" as used herein is defined as the compound or composition to be detected. This invention provides a method to detect an analyte having a specific functional group in a sample that also contains other species having the same functional group as the analyte, including a homolog of the analyte, by reversibly modifying the analyte under conditions wherein the homolog and other species present are not modified and which will allow for means of easily separating the modified analyte from the homolog and other species, converting the modified analyte back to the original analyte form, and detecting the analyte.

The term "capturing agent" is defined herein as a compound which will react with a specific functional group that is present on species present in the sample, including the homolog of the analyte, which is not present on the modified analyte. In the preferred embodiment, the capturing agent is a thiol-capturing agent, that is, any compound which is able to react with a free thiol group. Suitable thiol-capturing agents include, but are not limited to, α,β-unsaturated compounds such as maleimide and vinyl sulfone, and haloacetates such as iodoactetate. In one embodiment, the capturing agent is covalently or non-covalently coupled to a solid support.

The term "solid support" as defined herein is a porous or non-porous material that can have any one of a number of shapes, such as a strip, rod, particle, including beads and the like. Suitable materials for use in the present invention include, but are not limited to, controlled pore glass of various pore size and loading, polystyrene beads, polypropylene beads, magnetic beads, polyethylene glycol and cellulose.

The term "homogeneous method" as defined herein refers to any method for determining the presence and/or quantity of Hcy in a sample wherein the products of the thiol-containing compounds and the thiol-capturing agent are not removed from the sample.

The term "detection method" as defined herein is any means by which an analyte may be detected and/or quantitated. In one embodiment of the invention, the analyte detected and/or quantitated is Hcy. Suitable methods for detecting Hcy include photometric (e.g., calorimetric, spectrophotometric or fluorometric), electrochemical, chemiluminescent, radiolabel, GC, MS, GCMS, NMR and FTIR. In one embodiment, a colorimetric method for detecting the thiol group on Hcy is used. Suitable reagents for a calorimetric method include, but are not limited to, 5,5'- dithiobis(2-nitrobenzoic acid) (Ellman's reagent), monobromotrimethylammonio-bimane and related compounds.

In another embodiment of the invention, the analyte being detected and/or quantitated is Hcy thiolactone. In one embodiment, after the free thiol-containing compounds in the sample have reacted with the capturing agent, the amount of Hcy thiolactone in the remaining sample can be determined spectrophotometrically at 240 nm. This measurement will directly correspond to the amount of Hcy present in the sample.

The term "quenching reagent" as used herein is any reagent which is able to interact with a thiol-capturing agent such that the thiol-capturing agent is quenched and therefore unable to further react with free thiol-containing compounds. Examples of quenching reagents include dienes, reducing agents such as sodium borohydride and sodium cyanoborohydride, and halogens such as $I_2$, $Br_2$ and $Cl_2$.

The term "quench" as used herein means to inactivate a reagent.

The term "releasing agent" is a reagent capable of liberating the Hcy and other sulfur compounds from serum proteins and for reducing their disulfide forms. Suitable releasing agents are well known in the art and include, without limitation, reducing agents such as sodium and potassium borohydride, and sodium cyanoborohydride; thiols such as dithiothreitol (DTT), dithioerythritol, 2-mercaptoethanol, thioglycolic acid and glutathione; and phosphines and trialkylphosphines such as tri-n-butylphosphine and tris(2-carboxyethyl)phosphine, and free metals.

One embodiment of the invention involves a method for detecting the presence of Hcy in a sample that may contain Hcy, comprising the steps of (a) converting Hcy in a sample to Hcy thiolactone; (b) reacting free thiol-containing compounds in the sample with a thiol-capturing agent; (c) reconverting the Hcy thiolactone to Hcy; and (d) detecting the presence of Hcy. The conditions for converting Hcy to Hcy thiolactone are selected such that essentially all of the Hcy will convert to Hcy thiolactone within a short time, usually less than 30 minutes, preferably less than 5 minutes, and most preferably less than 1 minute. The conditions employed for converting Hcy to Hcy thiolactone are also selected such that Hcy will convert to Hcy thiolactone over a broad temperature range, preferably at ambient temperature. Suitable conditions for converting Hcy to Hcy thiolactone include the addition of a sufficient amount of a reagent to convert the pH of the sample to pH 0–5. Any reagent that can lower the pH of the sample to this range is suitable including, but not limited to, hydrochloric acid, perchloric acid, nitric acid, trichloroacetic acid and dichloroacetic acid.

In embodiments wherein the sample is a plasma sample, the preferred reagent for reducing the pH of the sample is trichloroacetic acid or perchloric acid. In this embodiment, the acid also serves to denature and precipitate proteins which may be present in the sample. This allows for a clean separation of the Hcy and other components from proteins in the sample.

In the methods of the present invention, the free thiol-containing compounds are reacted with a thiol-capturing agent, that is, any compound which is able to react with a free thiol group to eliminate reactive thiol groups in the sample. Suitable thiol-capturing agents include, but are not limited to, $\alpha,\beta$-unsaturated compounds such as maleimide and vinyl sulfone, and haloactetates such as iodoactetate.

In one embodiment, the thiol-capturing agent is bound to a solid support by methods known in the art. Example 5 describes a method for covalently binding maleimide to cellulose. In this example, maleic anhydride is converted to 6-maleimidoaminocaproic acid upon reaction with 6-aminocaproic acid and acetic anhydride. The 6-maleimidoaminocaproic acid is then converted to the corresponding acid chloride, which is then coupled to cellulose by the addition of a base. In embodiments wherein the thiol-capturing agent is bound to a solid support, the free thiol-containing compounds react with the thiol-capturing agent, and the products of this reaction are removed from the sample prior to determining the presence and/or quantity of Hcy in the sample.

In another embodiment, the method of detecting Hcy in a sample is a homogeneous method. In this embodiment, the thiol-capturing reagent reacts with free thiol-containing compounds, and any unreacted thiol-capturing agent in the sample is quenched with a quenching reagent prior to reconverting Hcy thiolactone to Hcy. In this embodiment it is not necessary to remove the products of the reaction between the thiol-capturing agent and non-Hcy thiol-containing compounds before the Hcy can be detected. If the thiol-capturing agent is an $\alpha,\beta$-unsaturated compound such as maleimide, quenching agents which will quench this agent include, but are not limited to, dienes, reducing agents and halogens. If the thiol-capturing agent is a haloacetate, quenching agents which will quench this agent include reducing agents.

The conditions for reconverting Hcy thiolactone to Hcy are selected so that Hcy thiolactone will reconvert to Hcy within a short time, usually less than 60 minutes, preferably less than 10 minutes, and most preferably less than 1 minute. The conditions are also selected so that Hcy thiolactone will reconvert to Hcy within a temperature range of 0–100° C., preferable within a temperature range of 37–80° C., and most preferably at ambient temperature. Suitable means for reconverting Hcy thiolactone to Hcy include adding reagents which will adjust the pH of the sample to pH 7–12, such as the addition of hydroxide ions, or by the addition of reducing reagents, provided that the reducing reagent does not contain thiol. The choice of reagents used to raise the pH of the sample and the desired pH range of the sample will depend on the choice of methods for detecting the Hcy present in the sample. For example, Ellman's reagent (5,5'-dithiobis(2-nitrobenzoic acid)) is a reagent known in the art for determining the presence of a free thiol group. Above a pH of 10, Ellman's reagent is unstable. Therefore, if Ellman's reagent is used as the detection method, the pH of the solution is kept below pH 10.

The present invention also provides a method for determining the presence and/or quantity of Hcy in a sample that may contain Hcy, comprising the steps of (a) converting Hcy in the sample to Hcy thiolactone; (b) reacting free thiol-containing compounds in the sample with a thiol-capturing agent; (c) reacting the Hcy thiolactone with a nucleophile; and (d) detecting the presence of the Hcy in the sample. In this embodiment, the Hcy thiolactone ring is opened by a nucleophile, such as an amine. This reaction produces an opened, derivatized Hcy having an exposed thiol group.

Once the open thiol form of Hcy or derivatized Hcy is present in the sample, the presence and/or quantity of Hcy in the sample can be determined. At this point, all free thiol-containing compounds other than Hcy have been removed from the sample. Therefore, once the Hcy thiolactone is reconverted to free reduced thiol Hcy or a derivatized Hcy, these forms of Hcy are essentially the only free reduced thiol-containing compound present in the sample. Therefore, by employing the methods of the present invention, the detection and/or quantitation of Hcy in a sample is greatly simplified in that any method which can detect and/or quantitate a free reduced thiol compound can be employed to determine the presence and/or quantity of Hcy in the sample. In one embodiment, photometric (e.g., calorimetric, spectrophotometric or fluorometric) detection methods may be employed to quantitate the amount of Hcy, as these methods may readily be adapted for routine use in clinical laboratories. In one embodiment of the present invention, Ellman's reagent is used as the detection agent. Ellman's reagent selectively reacts with free thiol groups to give the thionitrobenzoate anion. This ion is strongly colored ($\lambda_{max}$= 412 nm) and can serve as the basis for a quantitative spectrophotometric assay. The amount of the thionitrobenzoate anion produced is measured, and this measurement directly correlates to the free thiol content present in the eluent, which corresponds to the amount of Hcy which was present in the sample.

Hcy exists in human plasma as various mixed disulfides. Measurement of total Hcy in biological samples preferably involves a pretreatment step to form the free reduced-form Hcy. The preferred method of this invention measures the total Hcy, since the ratio of the three forms of Hcy (protein-bound, free-disulfide or free-reduced) is dependent on factors such as Hcy concentration, sample preparation, storage method, etc. However, measurement of free Hcy may be done without pretreatment, if desired.

To measure the total amount of Hcy in a sample, the sample is first combined with a releasing agent to release the Hcy from the circulating proteins as well as from Hcy dimers and other mixed disulfides. A particularly suitable releasing agent is a reducing agent, which reduces disulfides. One method of detecting for presence of Hcy in a sample which may contain Hcy, wherein at least a portion of the Hcy is in the disulfide form (protein-bound and free-disulfide), comprises the steps of (a) converting all disulfides to free thiol-containing compounds; (b) converting Hcy in the sample to Hcy thiolactone; (c) reacting free thiol-containing compounds in the sample with a thiol-capturing agent; (d) reconverting Hcy thiolactone to Hcy; and (e) detecting for the presence of Hcy in the sample.

The present invention also provides methods for determining the quantity of Hcy in a sample that may contain Hcy. One embodiment of the invention involves a method for determining the quantity of Hcy in a sample that may contain Hcy, comprising the steps of (a) converting the Hcy in a sample to Hcy thiolactone; (b) reacting the free thiol-containing compounds in the sample with a thiol-capturing agent; (c) reconverting Hcy thiolactone to Hcy; and (d) determining the absolute quantity of Hcy in the sample. In a preferred embodiment the capturing agent is bound to a solid support.

Yet another embodiment of the invention provides a method of determining the quantity of Hcy in a sample that may contain Hcy, wherein at least a portion of the Hcy is in the disulfide form (protein-bound and free-disulfide), and wherein the sample may contain other components which comprises the addition of a releasing agent to release the disulfide forms of thiol-containing compounds to the free thiol form.

Without wishing to limit the foregoing or to be bound by any theory, the following observations during certain steps of the assay of the invention (Hcy ring closure, bead capture of thiols and Hcy thiolactone ring opening) were made by the inventors:

As stated above, the ring closure of Hcy in a sample to Hcy-thiolactone occurs under acidic conditions (low pH). However, in certain circumstances, it was observed that in addition to lowering the pH of the sample, heating may be useful for efficient ring closure of Hcy to Hcy-thiolactone.

After conversion of Hcy in a sample to Hcy thiolactone, remaining thiols present in the sample are removed prior to determining the presence and/or amount of Hcy in the sample. In one embodiment, the thiols are removed by maleimide-derivatized cellulose beads. In certain circumstances, it was observed that the amount of Hcy detected after maleimide-cellulose bead capture of thiols was lower than expected. While not wishing to be bound by any theory, the inventors believe that the reduction of detectable Hcy may result from the continuous depletion of Hcy thiolactone during exposure to the maleimide-cellulose beads. As stated above, it was observed that the open Hcy and cyclic Hcy thiolactone forms exist in equilibrium. If any open Hcy form exists under the conditions of bead capture, it may react with and be captured by the maleimide-cellulose beads. According to the mass action principle, as open Hcy is depleted, closed Hcy thiolactone will convert to the open form of Hcy in an attempt to reestablish equilibrium. If this phenomenon takes place, a reduction of detectable Hcy may occur with increased exposure time to maleimide-cellulose beads.

Further, while bead capture of thiols with maleimide-cellulose beads is typically performed at pH 5.2 at elevated temperatures (e.g., 50° C.), it was observed that increasing the pH to 6.0–6.5 during maleimide-cellulose bead capture of thiols allowed the thiol capture to be performed at room temperature. However, under these circumstances, it was noted that increasing the pH may shift the equilibrium between the linear Hcy form and the cyclic Hcy thiolactone form toward the Hcy open form.

Hcy thiolactone present in a sample following bead capture of thiols may be reconverted to Hcy by increasing the pH of the sample to 9.0 or higher. It was observed that in certain circumstances the rate of Hcy thiolactone ring opening to Hcy required elevated temperatures, and that in other circumstances a pH greater than 9.0 may be required for efficient ring opening.

The method of the present invention allows for the rapid and easy detection and/or quantitation of Hcy in a sample. The following examples are provided for illustrative purposes only and are not intended to limit the scope of the invention.

Example 1 illustrates an example of an Hcy assay in which free thiol-containing compounds such as cysteine are removed from the sample by capture on a cellulose-anchored maleimide bead support.

Example 2 describes a kinetics study of the hydrolysis of Hcy thiolactone in order to determine the conditions necessary to convert Hcy thiolactone to Hcy for analysis.

In Example 3, varying concentrations of Hcy were mixed with constant amounts of Cys, and these mixtures were subjected to the same conditions for the Hcy assay, except for the maleimide capture of Cys, in order to determine the effects of the pH changes induced by the buffers on the analysis of Hcy. This study shows that the pH changes have no deleterious effect on the quantitation of Hcy.

Example 4 illustrates an assay of total Hcy in a sample wherein the free thiol-containing compounds (Cys) in the sample are captured by a cellulose-anchored maleimide bead support. This example shows that the successful assay of Hcy in the presence of a free thiol-containing compound (Cys).

Example 5 describes a method for covalently binding maleimide to a cellulose support.

Examples 6–27 describe variations of the assay of the present invention.

EXAMPLES

MATERIALS:

The following materials were used in the examples: PBS Buffer—pH 7.2, 1 mM EDTA (Baker 8993–01); homocysteine standard (Sigma H4628); homocysteine thiolactone HCl standard (Sigma H0376); physiological amino acid standard AN+ (Beckman #338156); TBP/DMF—10% Tri-n-butyl phosphine (SIGMA T 5277) in dimethylformamide (Sigma D8654); HEPES buffer—1 M HEPES (Sigma H3375), 20 mM EDTA, pH 8.0; CAPS buffer—1 M CAPS (Sigma C2632), 20 mM EDTA, pH 10.3; 7-fluorobenzo-2-oxa-1,3-diazole-4-sulfonate (SBDF) detection reagent - SBDF (Sigma F4383) in borate buffer pH 9.5 at 1 mg/mL; Centrex® filter—0.45 $\mu$m filter—Centrex® MF-5; Ellman's reagent (DTNB; 5,5'-dithio-bis-(2-nitrobenzoic acid); Pierce 22582); Ellman's reagent solution—10 mM DTNB in 25 mL absolute ethanol.

Example 1

A. Plasma Preparation, Reduction of Protein-bound Thiols and Precipitation of Plasma Proteins Human blood was collected into vacutainer tubes containing EDTA or heparin and immediately kept on ice. Plasma was separated from cells upon centrifugation at 2000×g for 5 min at 0–4° C. The separated plasma was kept on ice until further use. Dithiothreitol (DTT) was added to a final concentration of 5–50 mM to the plasma, the plasma was incubated at 37° C. for 15–30 min and then cooled on ice. An equal volume of ice-cold trichloroacetic acid (TCA) or $HClO_4$ was added to the plasma sample (either treated with DTT or not) and kept on ice for 15 min after thorough mixing. The sample was centrifuged for 10 min in a microcentrifuge and the supernatant was recovered.

B. Assay Protocol

The assay was initiated with 100 $\mu$L of TCA-precipitated plasma. To facilitate the maleimide capture of species containing reduced thiols in the plasma, the pH was increased to 5.1 by adding 60 $\mu$L of 3 M NaOAc (pH 6.5) buffer and 40 $\mu$L of water. An excess amount of cellulose-anchored maleimide bead support was added to this solution and the solution was incubated at 55° C. for 30 min with occasional mixing. The bead suspension was centrifuged, and 100 $\mu$L of the supernatant was recovered into a tube containing 500 $\mu$L of 0.5 M Tris, 20 mM EDTA (pH 9.9) buffer. To ensure ring opening of Hcy thiolactone in the basic medium (pH ~9.0), the solution was heated to 80° C. for 1 hr. After cooling to room temperature, 400 $\mu$L of 100 mM 5,5'-dithio-bis-(2-nitrobenzoic acid) (DTNB) solution was added and the absorbance was read within 15 min at 412 nm. To compensate for the buffer effects on DTNB itself, a solution containing 400 $\mu$L of 100 mM DTNB mixed with 600 $\mu$L of the Tris/EDTA buffer was used as a blank.

Example 2

Kinetics of Hcy Thiolactone Hydrolysis at Different pH Values and Temperatures.

Figure 2:
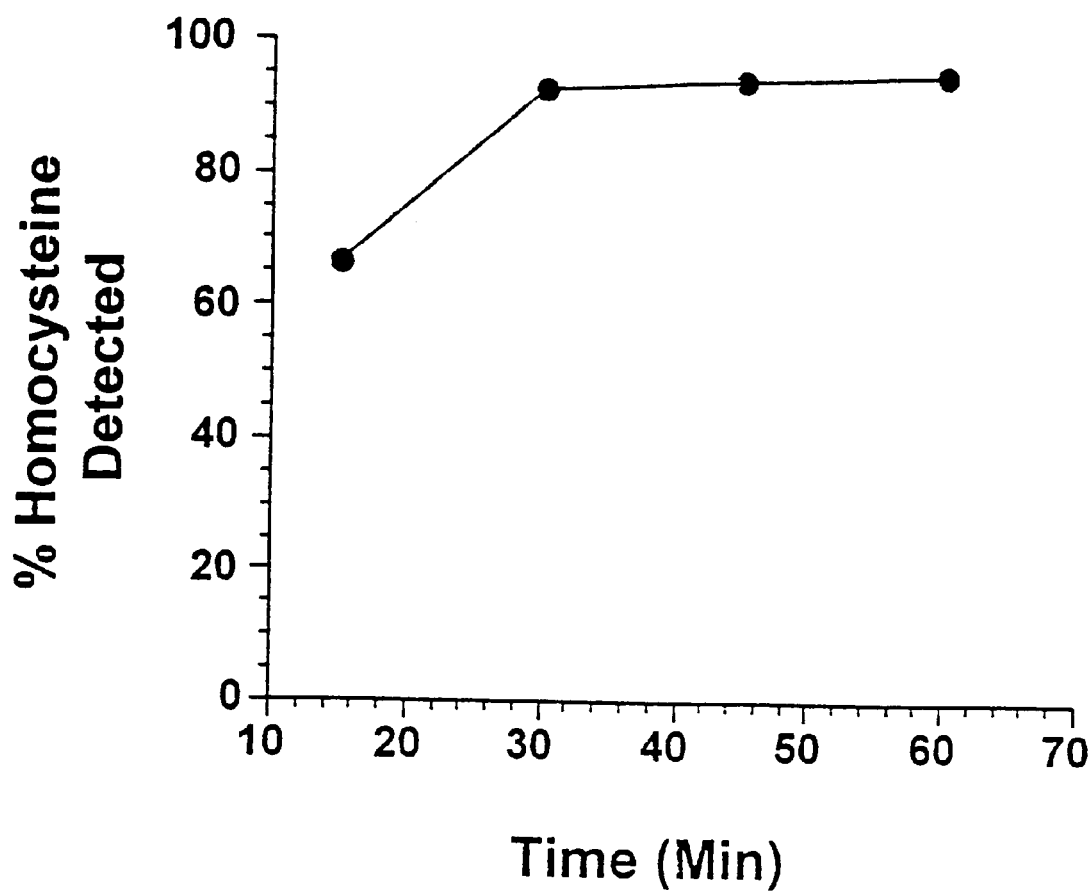
FIG. 2 depicts the percent Hcy thiolactone detected at various time points at 80° C. at pH 9.

Approximately 100 $\mu$M solution of Hcy thiolactone hydrochloride (Aldrich) prepared in 10 mM EDTA (pH. 4. 3) solution was used to measure the kinetics of opening of the thiolactone in 0.5 M Tris-HCl, 20 mM EDTA buffer at pH values of 8.6, 8.8 and 9.0. In this experiment, the reduced thiol group generated upon the opening of Hcy thiolactone was quantified using Ellman's reagent. As shown in FIG. 1, the ring opening of the Hcy thiolactone was not complete even after 45 min at 55° C. at all three of the pH's studied. Therefore, the ring opening reaction at 80° C. at pH 9 was investigated. Within 30 minutes of incubating at 80° C. the Hcy thiolactone was completely hydrolyzed (FIG. 2).

Example 3

Detecting Mixtures of Hcy and Cys Without Maleimide Capture.

Figure 3:
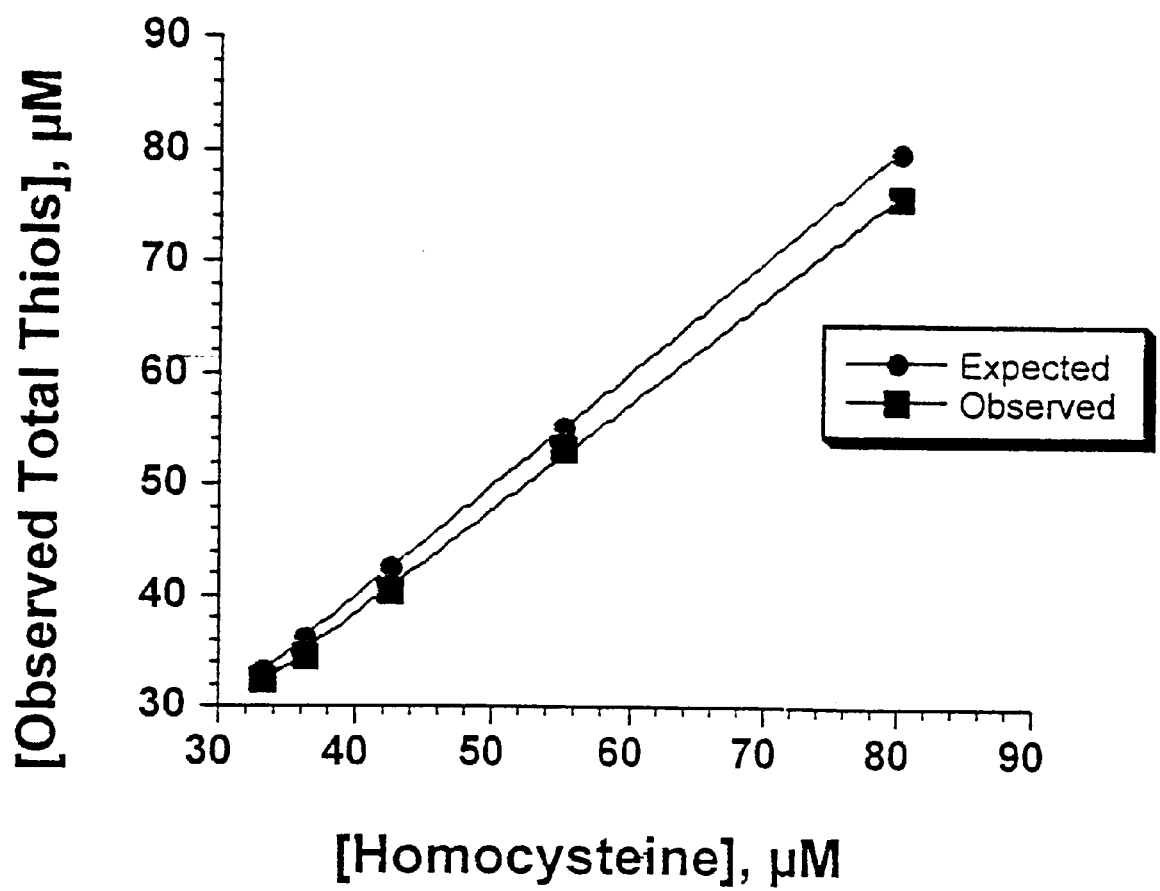
FIG. 3 depicts the observed total thiol concentration vs. Hcy concentration in samples containing varying concentrations of Hcy and constant concentrations of Cys without capturing Cys onto a maleimide support. The squares indicate the observed concentrations and the circles indicate the expected concentrations.

A varying concentration of Hcy thiolactone mixed with a constant amount of Cys (approximately 30 $\mu$M) in 10% TCA was subjected to all the steps in the assay protocol described in Example 1, except for maleimide capture. The resulting total thiols were estimated using Ellman's reagent. As a control, the total thiols of another set of mixtures was measured directly in 0.4 M Tris-HCl and 20 mM EDTA (pH 9.0) buffer, without subjecting the sample to initial acidification. As shown in FIG. 3, both measurements gave very similar values, indicating that the pH changes induced by the buffers used in the assay do not affect the thiol quantitation of Hcy and Cys.

Example 4

Specific Capture of Cys onto a Maleimide Support from Mixtures of Cys and Hcy

Figure 4:
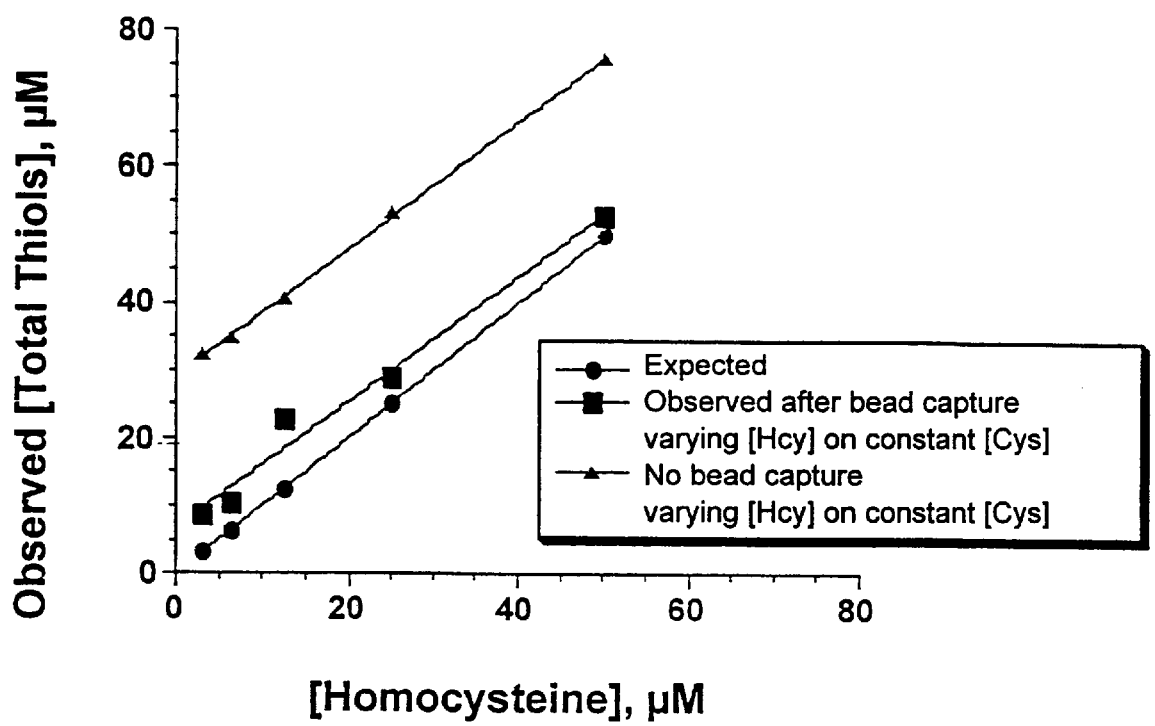
FIG. 4 depicts the observed total thiol concentration in samples containing varying concentrations of Hcy and constant concentrations of Cys after capture of Cys on a maleimide support. The circles indicate the expected concentrations, the squares indicate the observed concentrations after capture of the Cys on a maleimide support, and the triangles indicate the total thiol concentrations without capture of Cys on a maleimide support.

A varying concentration of Hcy thiolactone mixed with a constant amount of Cys was subjected to the complete assay protocol described in Example 1, including the maleimide bead capture. These mixtures were prepared in 10% TCA. In this procedure only Cys is expected to react with maleimide-anchored solid support, leaving Hcy thiolactone in the solution to be quantitated subsequently. As indicated in FIG. 4, the observed concentration of total thiols (squares) is very similar to the expected thiols derived from Hcy (circles), indicating that the thiol of Hcy was protected during the specific capture of Cys by maleimide. The total thiols measured in the absence of bead capture, in which the Hcy concentration was varied and the Cys concentration was held constant, gave higher values (triangles), which correspond to approximately 30 $\mu$M Cys in each sample. The results of this experiment show that all the chemical steps in the invention take place as proposed.

Example 5

Coupling Maleimide to a Cellulose Solid Support

Scheme 2 illustrates the coupling of maleimide to cellulose.

Preparation of 6-maleimidocaproic Acid (1):

A reaction mixture containing maleic anhydride and 6-aminocaproic acid in glacial acid was stirred at room temperature overnight. The solids which precipitated out of the reaction mixture were filtered, washed thoroughly with icy water to give 6-maleylaminocaproic acid, which was used without further purification. A reaction mixture of 6-maleylaminocaproic acid and sodium acetate in acetic anhydride was heated with stirring at 70–80° C. for 2 hours, then cooled to room temperature and the solids filtered. Acetic anhydride was removed under vacuum to give a yellow oil, which was purified by recrystallization to yield 6-maleimidocaproic acid (1) as white powder.

Procedure for loading the cellulose support (3):

Oxalyl chloride was added to 6-maleimidocaproic acid (1) at room temperature. The clear solution was stirred at room temperature for 30 minutes and then at 60–70° C. for 3 hours. Excess oxalyl chloride was removed under vacuum to give yellow crystals (2), which were dissolved in anhydrous DMF. Cellulose was added to the reaction mixture, followed by pyridine and the mixture was stirred at room temperature overnight. The modified cellulose (3) was filtered, washed with DMF, $CH_3OH$, $CH_3CN$ and ethyl ether, and dried under high vacuum.

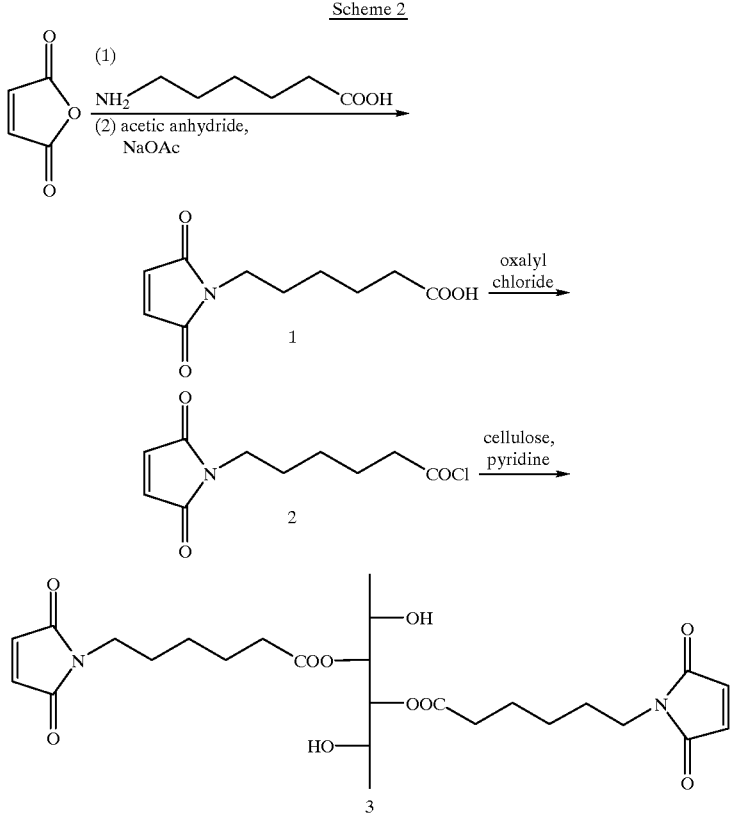

Scheme 2

Example 6
Hcy Ring Closure at Room Temperature

The open form of Hcy (Hcy-open) was suspended in 10% TCA solution and kept at room temperature for 30 minutes. The level of quantifiable thiols were measured using Ellman's reagent in pH 9.0 buffer. Under these conditions only the open form of Hcy was detected. The detected values of thiols using Hcy suspended in 10% TCA were identical to those obtained with Hcy suspended in water.

Example 7
Hcy Ring Closure at Elevated Temperature

Figure 5:
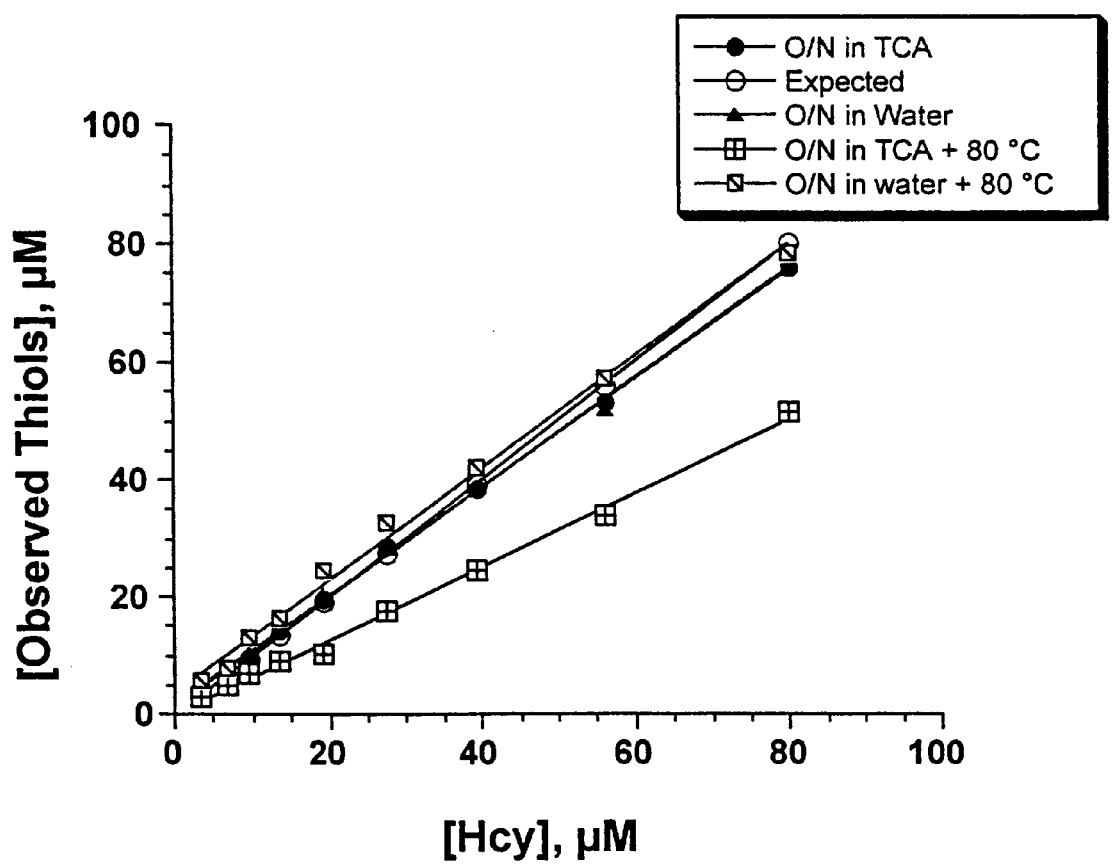
FIG. 5 shows the concentration of observed thiols as a function of varying concentrations of Hcy. Closed circles and triangles indicate detected thiols in 10% TCA and in water, respectively, without heating. Crossed squares indicate the values obtained after heating at 80° C. in 10% TCA solution, and slashed squares indicate the values obtained in water after the same treatment.

Varying concentrations of Hcy-open were suspended in either water or 10% TCA solution and left overnight at room temperature. Half of these samples were heated at 80° C. for 30 minutes. Thiol contents of these solutions were determined using Ellman's reagent. The results are shown in FIG. 5. Open circles indicate expected concentrations of Hcy. Closed circles and triangles indicate detected thiols in the samples in 10% TCA and in water, respectively, left overnight without heating. In these samples the level of quantifiable thiols in TCA were identical to those in water. However, upon heating at 80° C. for 30 minutes, significantly decreased level of thiols were observed in Hcy suspended in TCA (crossed squares), but not in water (slashed squares) indicating that in addition to low pH medium, heating may be required for the ring closure of Hcy.

Example 8
Efficiency of Hcy Ring Closure in HCl vs. TCA

Figure 6A:
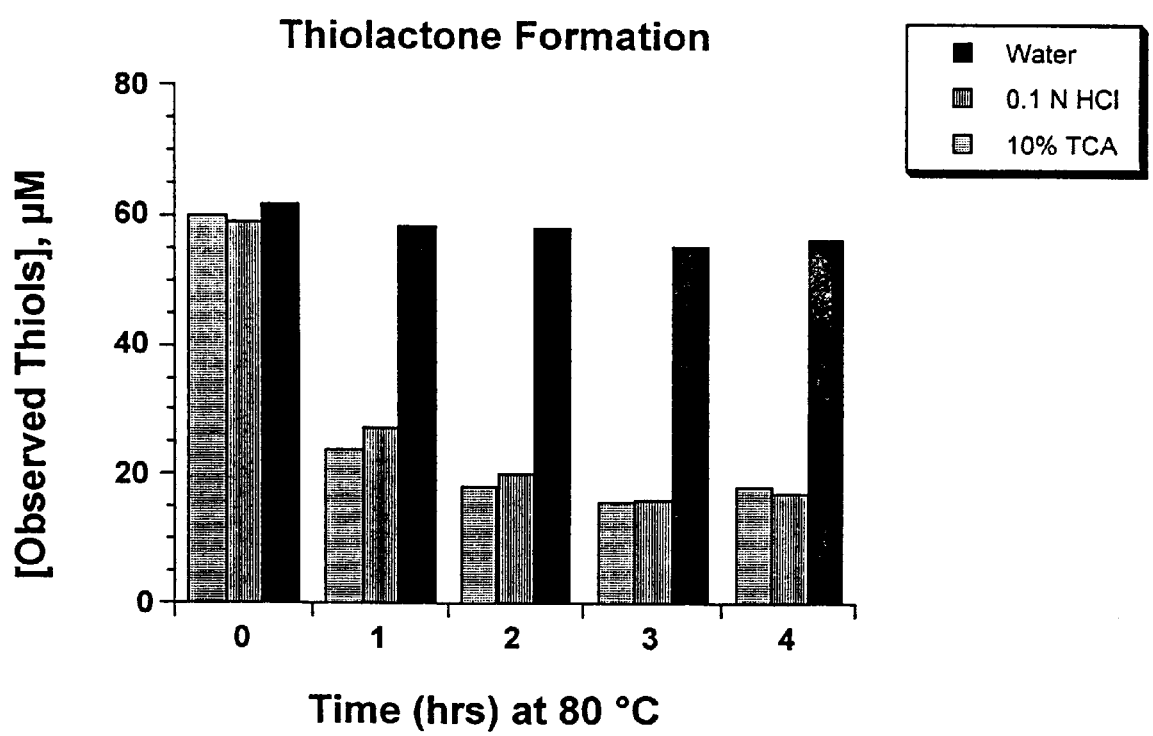
FIG. 6A shows the concentration of observed thiols expressed as a function of incubation time for fixed concentrations of Hcy suspended in water (filled), 10% TCA (vertical striped) or 0.1 N HCl (horizontal stripes).
Figure 6B:
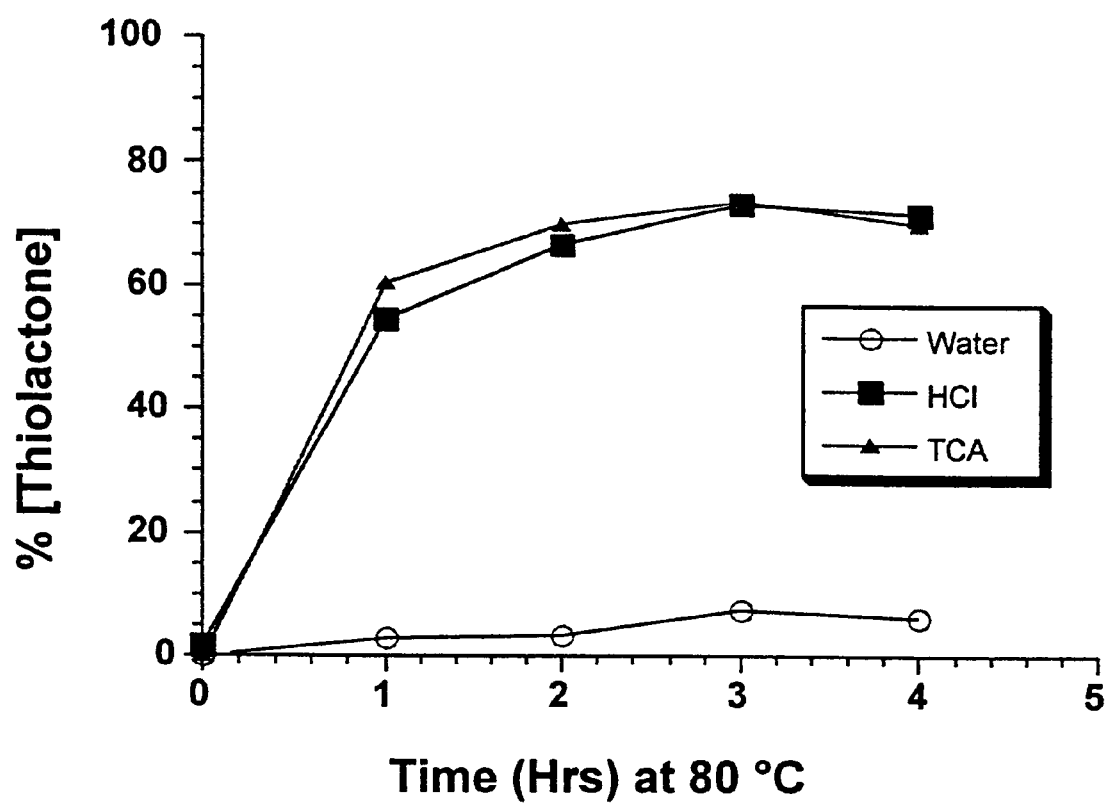
FIG. 6B shows the per cent Hcy thiolactone formed as a function of incubation time fixed concentrations of Hcy suspended in water (circles), 10% TCA (triangles) or 0.1 N HCl (squares).

The efficiency and kinetics of ring closure of Hcy to Hcy thiolactone in different acidic environments at 80° C. was studied. A fixed concentration of Hcy-open (60 $\mu$M) was suspended in either water, 0.1 N HCl or 10% TCA and heated at 80° C. for up to 4 hours. The thiol content was determined using Ellman's reagent. The concentration of observed thiols expressed as a function of incubation time are shown in FIG. 6A. Ring closure takes place with similar efficiency in 0.1 N HCl (FIG. 6A, horizontal stripes) and 10% TCA (0.6 N) (FIG. 6A, vertical stripes). Presumably due to the complete ionization of HCl, lower concentration of HCl (0.1 N) is more effective than 10% (0.6 N) TCA. FIG. 6B shows the percent Hcy thiolactone formed as a function of incubation time. About 70% of Hcy is converted to the thiolactone when incubated at 80° C. for 3 hours in the acidic environment. Even after 4 hours at 80° C., Hcy did not undergo ring closure in water, indicating the requirement of low pH.

Example 9
Hcy Ring Closure in HClO$_4$ vs. TCA

Figure 7:
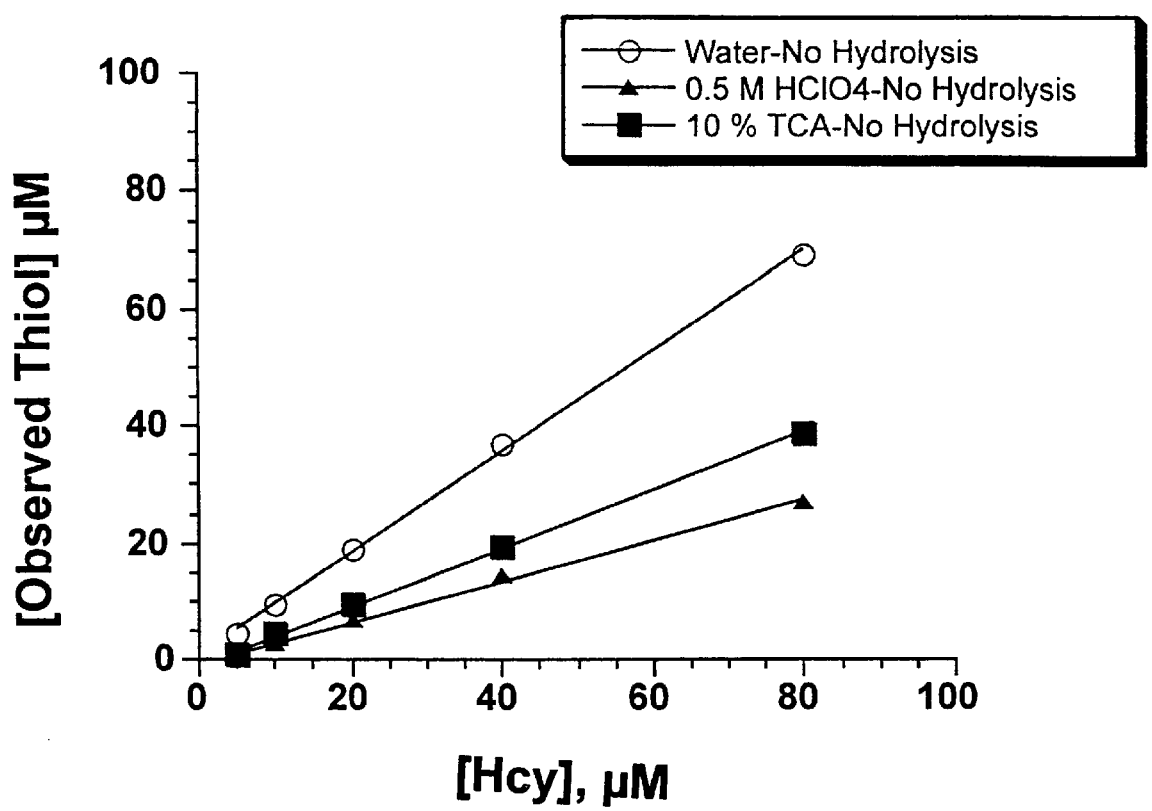
FIG. 7 shows the concentration of observed thiols as a function of concentration of Hcy for varying concentrations of Hcy spiked into water (circles), 0.5 M $HClO_4$ (triangles) or 10% TCA (squares) after heating to 80° C. for 1.5 hours.

In addition to TCA, HClO$_4$ can be used to remove plasma proteins by precipitation. The extent of ring closure of Hcy in 0.5 M HClO$_4$ solution was investigated and compared to that in 0.6 M TCA (10% TCA). Varying concentrations of Hcy-open were spiked into either 10% (0.6 M) TCA solution or 5% (0.5 M) HClO$_4$ solution and heated to 80° C. for 1.5 hours. The thiol content was determined using Ellman's reagent. As summarized in FIG. 7, the efficiency of ring closure is even better in 0.5 M HClO$_4$ (closed triangles) than in 0.6 M TCA (closed squares). The open circles indicate controls where Hcy was suspended in water and was not heated. However, even after heating at 80° C. in 0.5 M HClO$_4$ for 1.5 hours the efficiency of ring closure is not 100%.

Figure 8A:
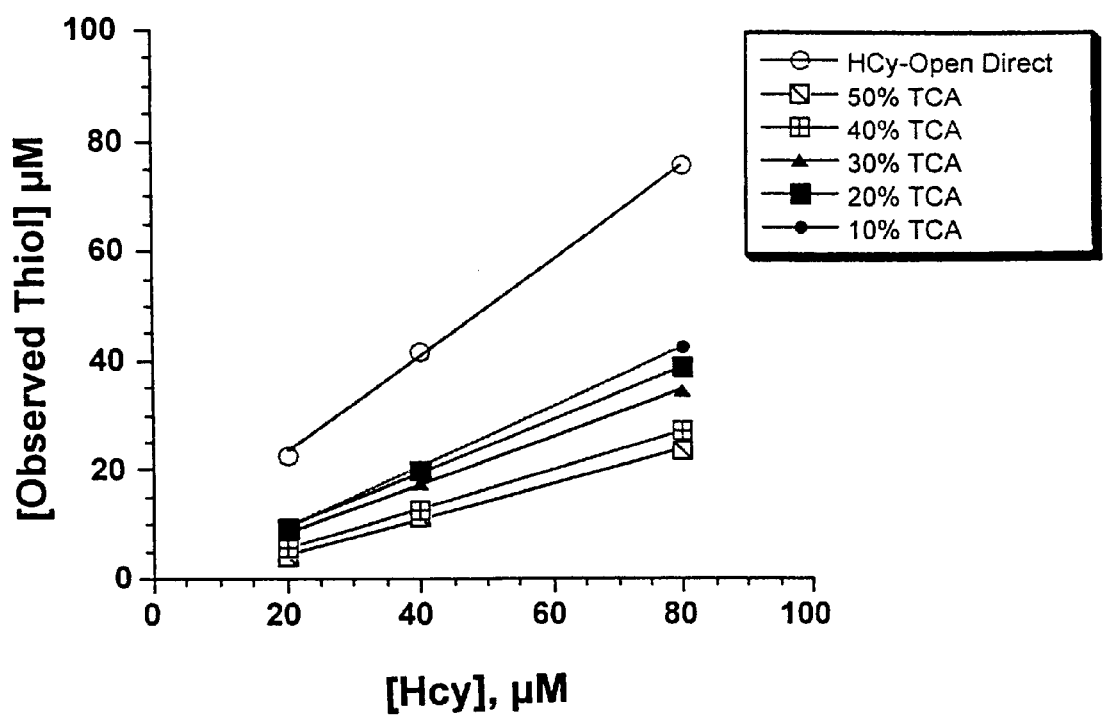
FIG. 8A shows the concentration of observed thiols as a function of Hcy concentration for varying concentrations heated to 80° C. for 2 hours in varying concentrations of TCA. Open circles are controls where Hcy was suspended in water and not heated, slashed squares=50% TCA, crossed squares=40% TCA, closed triangles=30% TCA, closed squares=20% TCA, closed circles=10% TCA.
Figure 8B:
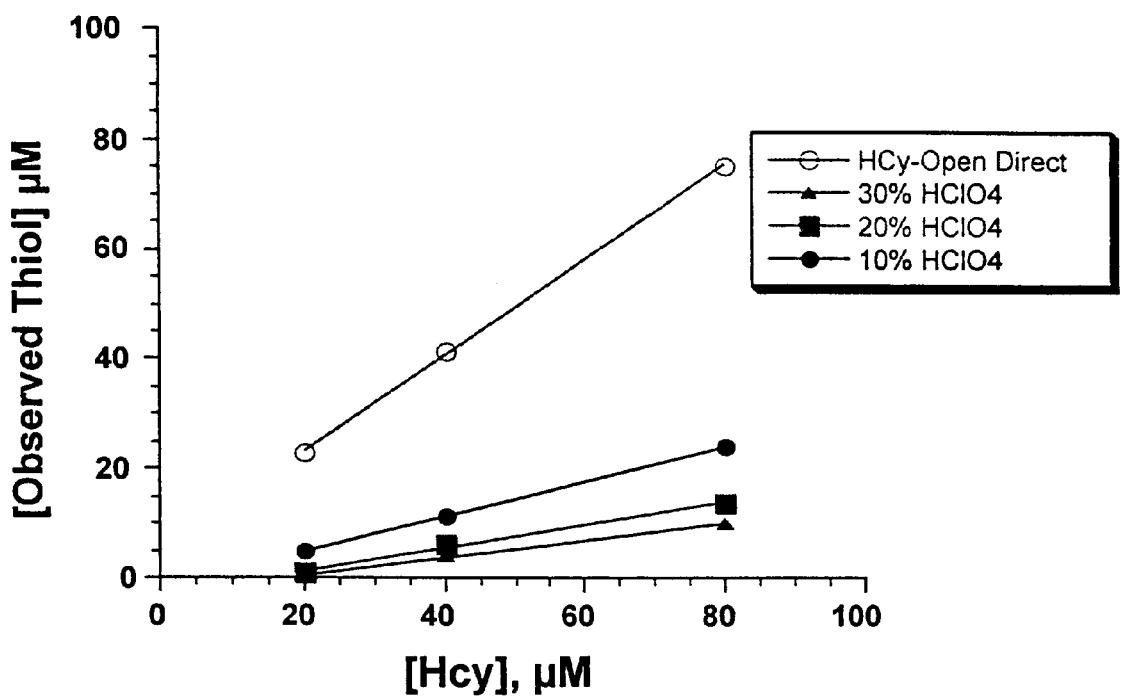
FIG. 8B shows the concentration of observed thiols as a finction of Hcy concentration for varying concentrations heated to 80° C. for 2 hours in varying concentrations of $HClO_4$. Open circles are controls where Hcy was suspended in water and not heated, closed triangles=30% $HClO_4$, closed squares=20% $HClO_4$, closed circles=10% $HClO_4$.

The ring closure efficiency in plasma precipitated with increasing concentrations of either TCA or $HClO_4$ was then investigated (FIGS. 8A and 8B). In these experiments, plasma samples were prepared as in Example IA. Varying concentrations of Hcy-open were spiked into either 10%–50% TCA solutions (FIG. 8A) or into 10% - 30% $HClO_4$ solution (FIG. 8B). These Hcy solutions were heated at 80° C. for 2 hours before quantification of thiols with Ellman's reagent. The open circles in FIGS. 8A and 8B indicate the controls where Hcy was resuspended in water and was not heated. In both cases an increase in the concentration of acid increased the amount of Hcy thiolactone formed. As noted above, the efficiency of Hcy thiolactone formation in $HClO_4$ is higher than that in TCA (50% TCA and 30% $HClO_4$ are 3 M with respect to each acid).

Example 10
Incubation of Hcy and Hcy Thiolactone in Acid

Figure 9:
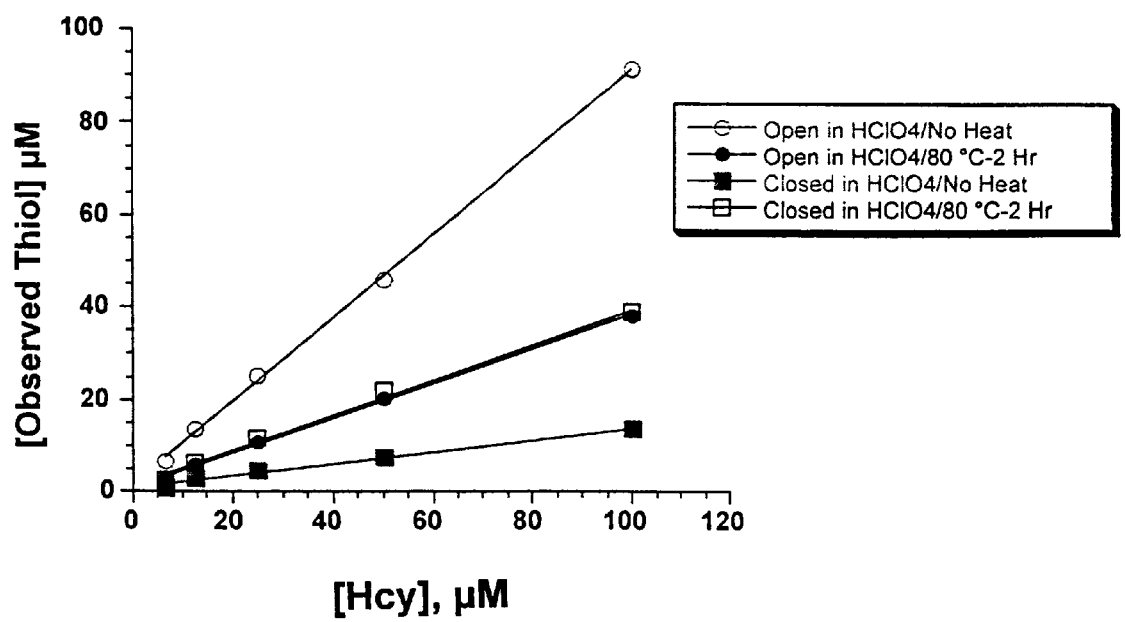
FIG. 9 shows the concentration of observed thiols as a function of Hcy concentration for varying concentrations of Hcy (Hcy-open) and Hcy thiolactone (Hcy-closed) spiked into $HClO_4$ and incubated at room temperature or at 80° C. for 2 hours. Open circles=open Hcy at rt, closed circles= open Hcy at 80° C., closed squares=Hcy thiolactone at rt, open squares=Hcy thiolactone at 80° C.
Figure 10:
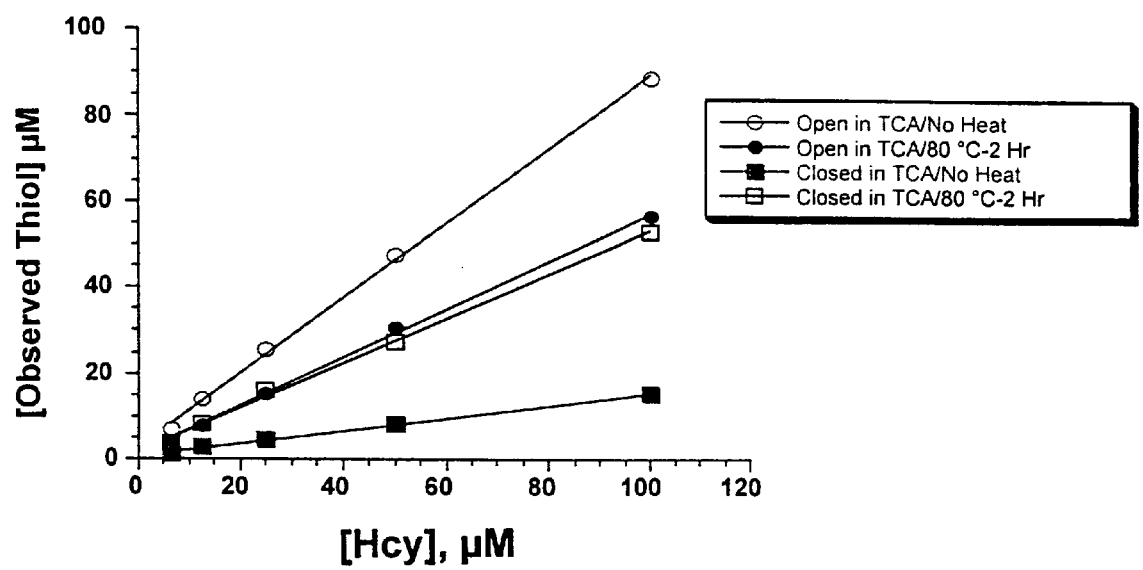
FIG. 10 shows the concentration of observed thiols as a function of Hcy concentration for varying concentrations of Hcy (Hcy-open) and Hcy thiolactone (Hcy-closed) spiked into TCA and incubated at room temperature or at 80° C. for 2 hours. Open circles=open Hcy at rt, closed circles=open Hcy at 80° C., closed squares=Hcy thiolactone at rt, open squares=Hcy thiolactone at 80° C.

To further understand ring closure of Hcy, the following equilibrium experiment was carried out. The results are summarized in FIGS. 9 and 10. Varying concentrations of Hcy-open (FIGS. 9 and 10, open and closed circles) and Hcy thiolactone (FIGS. 9 and 10, open and closed squares) were separately spiked into either 8% $HClO_4$ solution (FIG. 9) or 10% TCA solution (FIG. 10). These solutions were either incubated at room temperature or heated at 80° C. for 2 hours. The thiol content in each sample was determined using Ellman's reagent. In both cases, i.e. starting with either the open form of Hcy or the Hcy thiolactone, equal amounts of thiols were detectable (FIGS. 9 and 10, open squares and closed circles), indicating an establishment of an equilibrium between the open and closed forms. The equilibria established in these two acidic solutions are different as characterized by the fractions of open and closed forms. The fraction of Hcy in the Hcy thiolactone form in 8% $HClO_4$ (0.8 N) and 10% TCA (0.6 N) is 0.56 and 0.38, respectively. Identical experiments were carried out in plasma that has been precipitated with 1 N TCA, 1 N $HClO_4$ and 1 N $HClO_4$+1 N HCl. The estimated fraction of Hcy in the Hcy thiolactone form in plasma under these conditions is as follows:

In 1 N TCA=0.64±0.93

In 1 N $HClO_4$=0.70±0.10

In 1 N $HClO_4$+1 N HCl=0.70±0.15

Example 11
Removal of DTT by Maleimide-cellulose Beads

After Hcy in a sample is converted to Hcy thiolactone, the sample may also contain mM concentrations of DTT (a thiol-containing compound) used for reduction and/or a mixture of other molecules with and without thiol groups. It is desirable to remove all interfering thiol-containing compounds from the solution prior to measuring the presence and/or amount of Hcy in the sample. In this example, the removal of thiol-containing compounds was achieved using maleimide anchored to a solid support (maleimide-cellulose beads; see Example 5) as the thiol-capturing agent.

To analyze the total Hcy levels, 2.5 mM dithiothreitol (DTT) was used to liberate protein-bound homocysteine into plasma and the precipitated proteins were removed by centrifugation. The initial reduction with DTT demands that all DTT be captured and removed by maleimide beads for accurate quantification of Hcy concentration in a sample. Low $\mu M$ concentrations of thiol containing compounds such as cysteine and glutathione were effectively captured by maleimide anchored onto cellulose beads (maleimide-cellulose beads batch #1) at 50° C. for 30 minutes in pH 5.2 buffer. However, bead batch #1 was not effective in capturing and removing all DTT. Based on this observation, a new batch (batch #2) of maleimide-cellulose beads with high-loading was prepared. The maleimide-cellulose bead capture step was performed at 50° C. for 30 minutes in pH 5.2 buffer. These conditions were chosen to effectively capture mM concentrations of DTT and also to preserve the integrity of Hcy thiolactone. Under these conditions the new bead preparation (batch #2) with high maleimide loading efficiently captured mM concentrations of DTT.

Example 12
Detection of Hcy in the Presence of DTT

Figure 11:
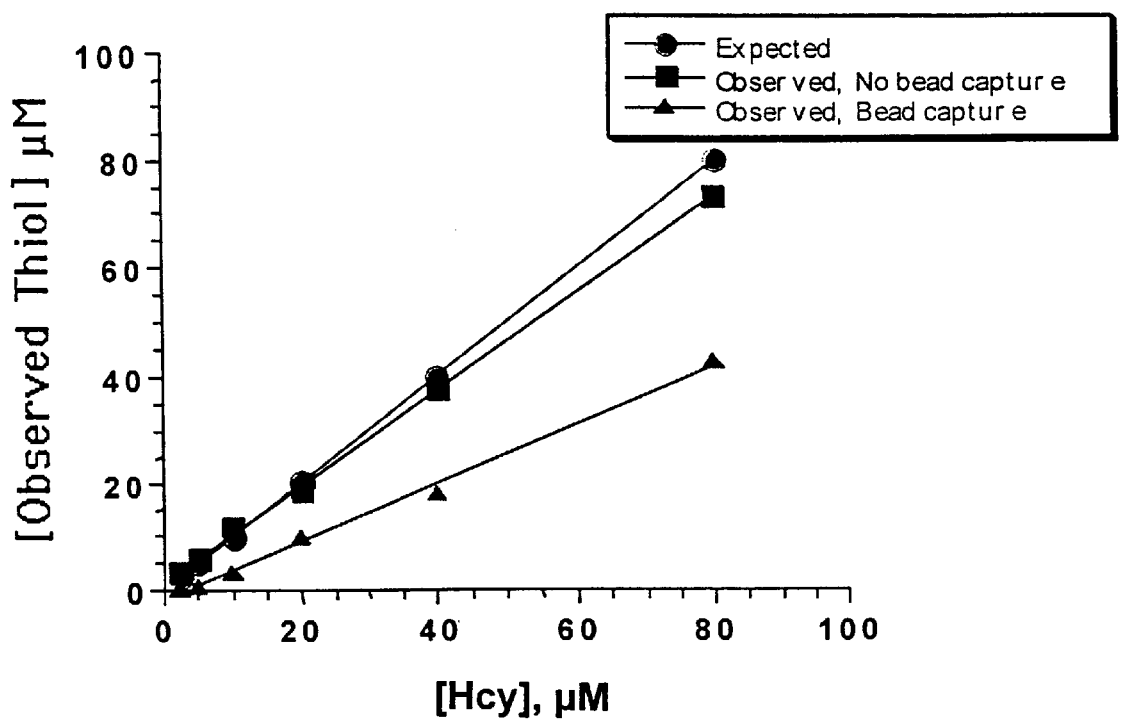
FIG. 11 shows the concentration of observed thiols as a function of Hcy concentration for varying concentrations of Hcy thiolactone spiked into 10% TCA containing 2.5 mM DTT, followed by capture of DTT with maleimide-cellulose beads. Closed circles indicate expected concentrations, closed squares indicate observed values without bead capture and closed triangles indicate closed triangles with bead capture.

The feasibility of the specific detection of $\mu M$ concentrations of Hcy thiolactone in the presence of mM concentrations of DTT was investigated. Varying concentrations of Hcy thiolactone were spiked into a 10% TCA solution containing 2.5 mM DTT. The pH of the solution was increased to pH 5.2 with 3 M NaOAc (pH 6.5) and maleimide-cellulose bead capture was performed at 50° C. for 1 hour. Beads were removed by centrifugation, and the pH of the supernatant was increased to pH 9.5 with a buffer consisting of 0.5 M Tris and 20 mM EDTA (pH 9.48) and heated for 1 hour at 80° C. Thiols were quantified using Ellman's reagent. Values observed with and without bead capture are shown in FIG. 11 by triangles and squares, respectively. Expected concentrations of Hcy are indicated by circles. As shown in FIG. 11, maleimide-cellulose beads captured DTT effectively, leaving Hcy thiolactone to be detected. However, the quantity of Hcy detected after the bead capture was lower than the expected values. This observation has been reproducible both in buffer and in plasma.

Example 13
Efficiency of Thiol Capture by Maleimide-cellulose Beads as a Function of Temperature Studies described earlier indicated that Hcy exists in both open and closed form, but not exclusively in one form or the other. The fraction of each form depends on the environment.

Figure 12:
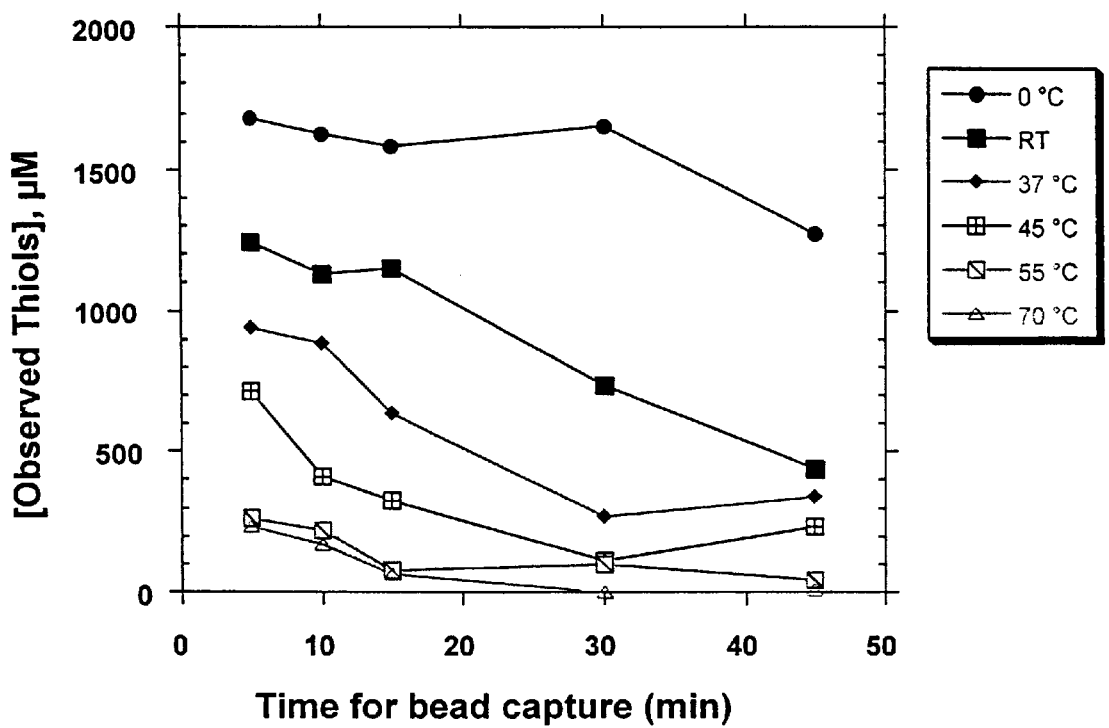
FIG. 12 shows the concentration of observed thiols as a function of time for thiol capture with maleimide-cellulose beads at various temperatures. Closed circles=0° C., closed squares=rt, diamonds=37° C., crossed squares=45° C., slashed squares=55° C., open triangles=70° C.

Maleimide-cellulose bead capture efficiency at pH 5.2 was investigated as a function of temperature. A solution of 10% TCA containing 2.5 mM DTT was used in this experiment. After adjusting the pH of this solution to 5.2 with 3 M NaOAc buffer (pH 6.5), maleimide-cellulose beads (80–90 mg) were added and thiol capture was performed at various temperatures. Samples were taken at several time points and the supernatants were recovered by centrifugation. Thiols remaining after bead capture were quantified using Ellman's reagent. An efficient removal of DTT by bead capture was seen at temperatures above 50° C. at pH 5.2 (this is the pH of the medium used for bead capture) (FIG. 12). Subsequently, it was discovered that efficient bead capture at room temperature over 30 minutes was possible when the pH was increased approximately by 1 unit (pH 6.0–6.5).

Example 14
Thiol Capture by Maleimide-cellulose Beads as a Function of Time

Figure 13:
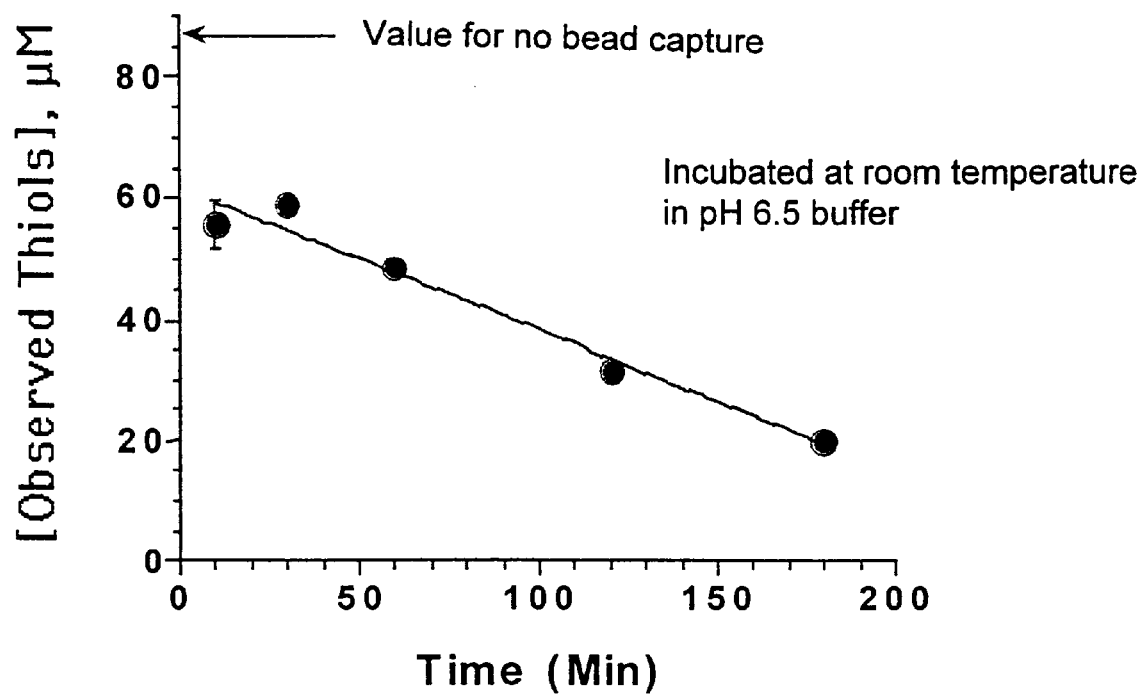
FIG. 13 shows the concentration of observed thiols as a function of incubation time with maleimide-cellulose beads at room temperature in pH 6.5 buffer.

In this example, the effects on the outcome of the bead capture results as a function of time the solution is contacted with maleimide-cellulose beads was studied. A fixed concentration of Hcy thiolactone (80 $\mu M$) in 10% TCA was used in this experiment. After adjusting the pH of this solution to 6.5 with 1 M HEPES buffer (pH 8.04), maleimide-cellulose beads (80–90 mg) were added and thiol capture was performed at room temperature. Samples were taken at various time points and the supernatants were recovered by centrifugation. The pH of the supernatant of each sample was increased to 9.5 with a buffer consisting of 1 M CAPS and 20 mM EDTA (pH 10.3) and incubated at 80° C. for 45 minutes. Thiols remaining after bead capture were quantified with Ellman's reagent. As indicated in FIG. 13, quantifiable Hcy concentration decreases with the increase in incubation time with the beads. Approximately 62% of Hcy is detected even after 10 minutes of bead capture at pH 6.5.

Example 15
Effects of pH on Maleimide-cellulose Bead Capture

Figure 14:
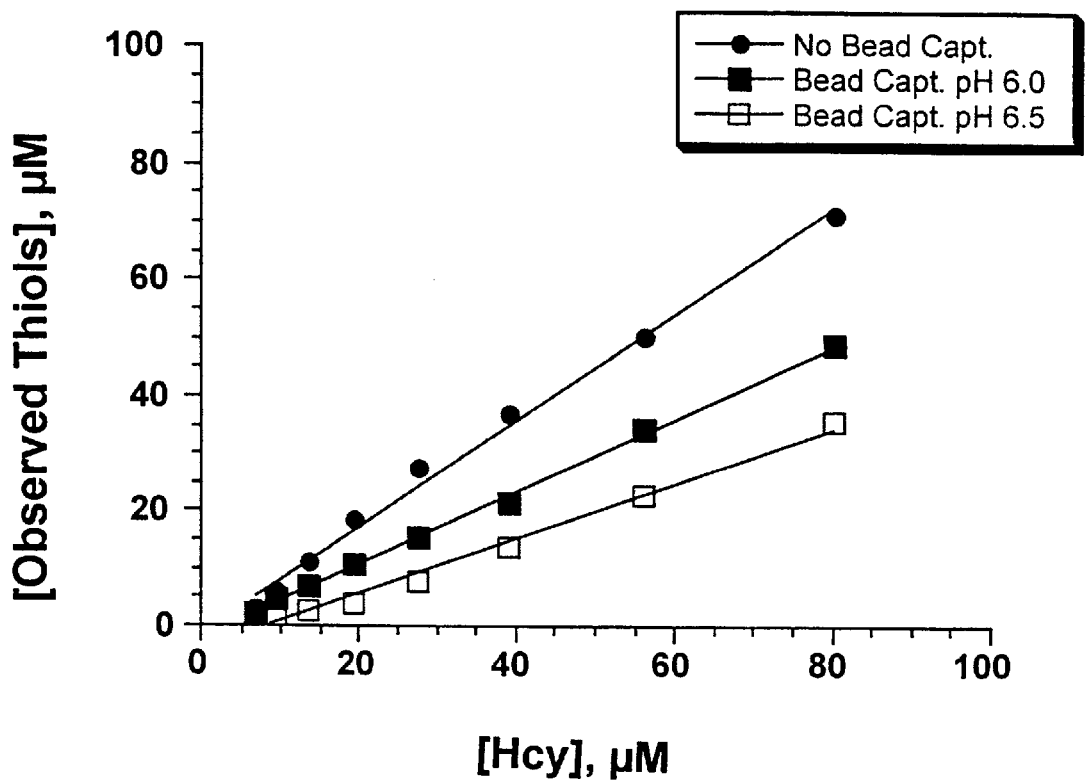
FIG. 14 shows the concentration of observed thiols as a function of concentration of Hcy for bead capture at pH 6.0 (closed squares) and pH 6.5 (open squares). Closed circles indicate observed values without bead capture.

The effects of decreasing the pH of the samples during the bead capture were studied. In this experiment, varying concentrations of Hcy thiolactone were spiked into 10% TCA solution containing 2.5 mM DTT. The pH of the solution was increased to either 6.0 or 6.5 with 1 M HEPES buffer (pH 8.04), and maleimide-cellulose bead capture was performed at room temperature for 20 minutes. Beads were removed by centrifugation. The pH of the supernatant was increased to 9.5 with a buffer consisting of 1 M CAPS and 20 mM EDTA (pH 10.3) and incubated at 80° C. for 45 minutes. Thiols remaining after bead capture were quantified with Ellman's reagent. The results are summarized in FIG. 14. Observed values without bead capture are indicated by closed circles. The decrease in pH from 6.5 (open squares) to 6.0 (closed squares) increased the level of detected Hcy.

Example 16
Ring opening of Hcy Thiolactone

Figure 15:
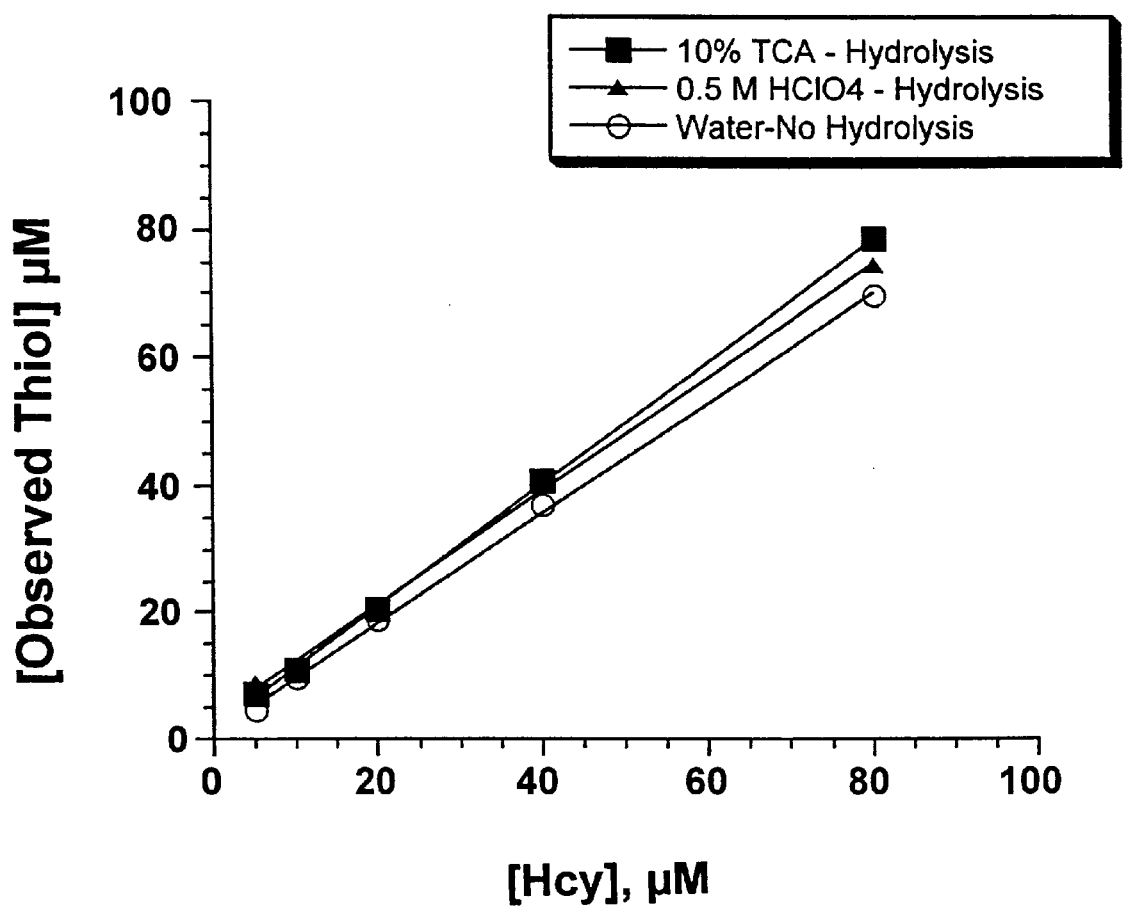
FIG. 15 shows the concentration of observed thiols as a function of Hcy concentration. Varying concentrations of Hcy-open were spiked into either 10% TCA (squares) or 0.5 M HClO4 (triangles) and incubated at 80° C. for 1.5 hours. The pH of the solution was increased to 6.5 with 1 M HEPES buffer (pH 8.04), and then to 9.5 with a buffer consisting of 1 M CAPS and 20 mM EDTA (pH 10.3). Samples were incubated at 80° C. for 45 minutes.

The rate of ring opening of the thiolactone was observed to be pH dependent when measured in sodium borate solution. The $t_{1/2}$ value for ring opening in 20 mM sodium borate and 200 mM NaCl solution at pH 9.3 is 3.7 minutes at 82° C. Varying concentrations of Hcy-open were spiked into either 10% TCA or 5% $HClO_4$ and incubated at 80° C. for 1.5 hours. The pH of the solution was increased to 6.5 with 1 M HEPES buffer (pH 8.04), and then to 9.5 with a buffer consisting of 1 M CAPS and 20 mM EDTA (pH 10.3). Samples were incubated at 80° C. for 45 minutes. The thiol content was determined with Ellman's reagent. The results are summarized in FIG. 15. Complete ring opening of Hcy thiolactone suspended in both 10% TCA (closed squares) and 8% $HClO_4$ (closed triangles) solutions was observed after adjusting the pH of the samples to 9.5 (with 1 M CAPS buffer) and at incubating at 80° C. Open circles indicate controls where Hcy-open was suspended in water and used for thiol determination without pH shift or heat treatments.

Example 17
Efficiency of Hcy Thiolactone Ring Opening in Plasma Samples

Figure 16:
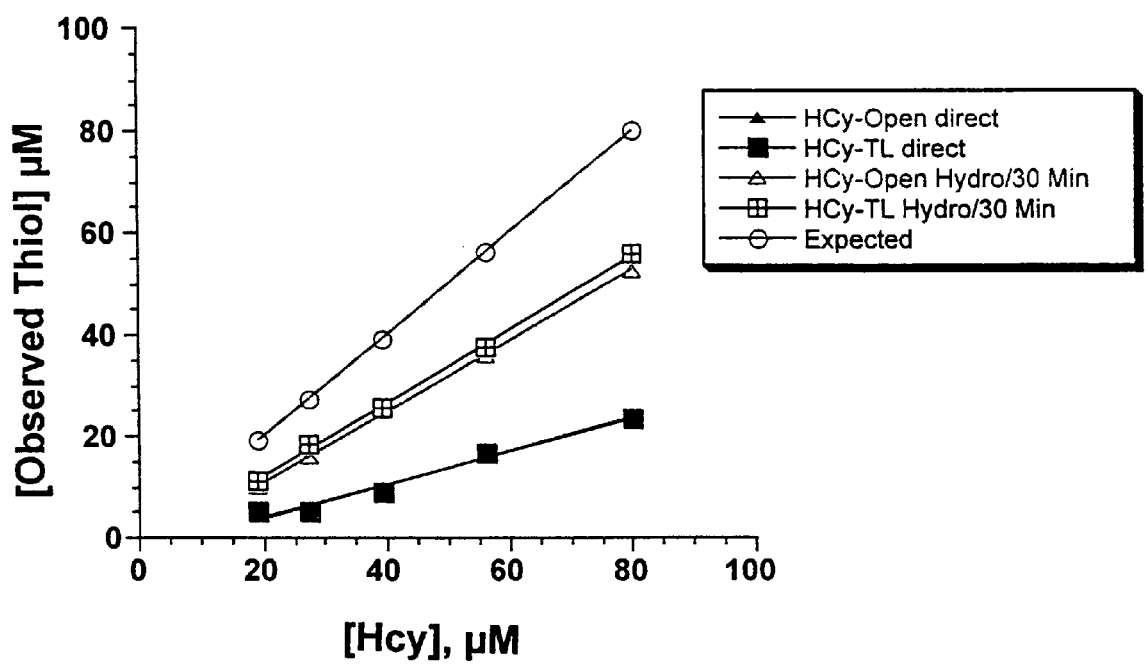
FIG. 16 shows the concentration of observed thiols as a function of Hcy concentration. Varying concentrations of Hcy-open (triangles) and Hcy-closed (squares) were spiked into a plasma sample that had been precipitated with 8% $HClO_4$. Samples were incubated at 80° C. for 2 hours, the pH of the samples was increased to 6.5 with 1 M HEPES buffer (pH 8.04), and then to 9.5 with a buffer consisting of 1 M CAPS and 20 mM EDTA (pH 10.3). The thiol content was determined with the Ellman's reagent after incubation at 80° C. for 45 minutes (open squares and triangles) or without incubation (closed squares and triangles). Open circles indicate controls where Hcy-open was suspended in water and used for thiol determination without pH shift or heat treatments.

The efficiency of Hcy thiolactone ring opening in plasma sample was investigated. The results are summarized in FIG. 16. Varying concentrations of Hcy-open (triangles) and Hcy thiolactone (squares) were separately spiked into plasma samples that had been precipitated with 8% $HClO_4$ as described in Example 1A. These plasma samples were incubated at 80° C. for 2 hours to establish equilibrium. The pH of the samples was then increased to 6.5 with 1 M HEPES buffer (pH 8.04), and then to 9.5 with a buffer consisting of 1 M CAPS and 20 mM EDTA (pH 10.3). The thiol content of each sample was then determined either directly (i.e., no incubation) (FIG. 16, closed squares and closed triangles) or after incubation at 80° C. for 45 minutes (FIG. 16, crossed squares and open triangles). Open circles in FIG. 16 indicate controls where Hcy-open was suspended in water and used for thiol determination without pH shift or heat treatment. The thiol content in each sample was determined with Ellman's reagent.

In plasma, the efficiency of ring opening was observed to be substantially lower than that observed in solution (see, Example 16). This observation is true whether the plasma used was precipitated with TCA or $HClO_4$.

Example 18
Kinetics of Hcy Thiolactone Ring Opening

Figure 17A:
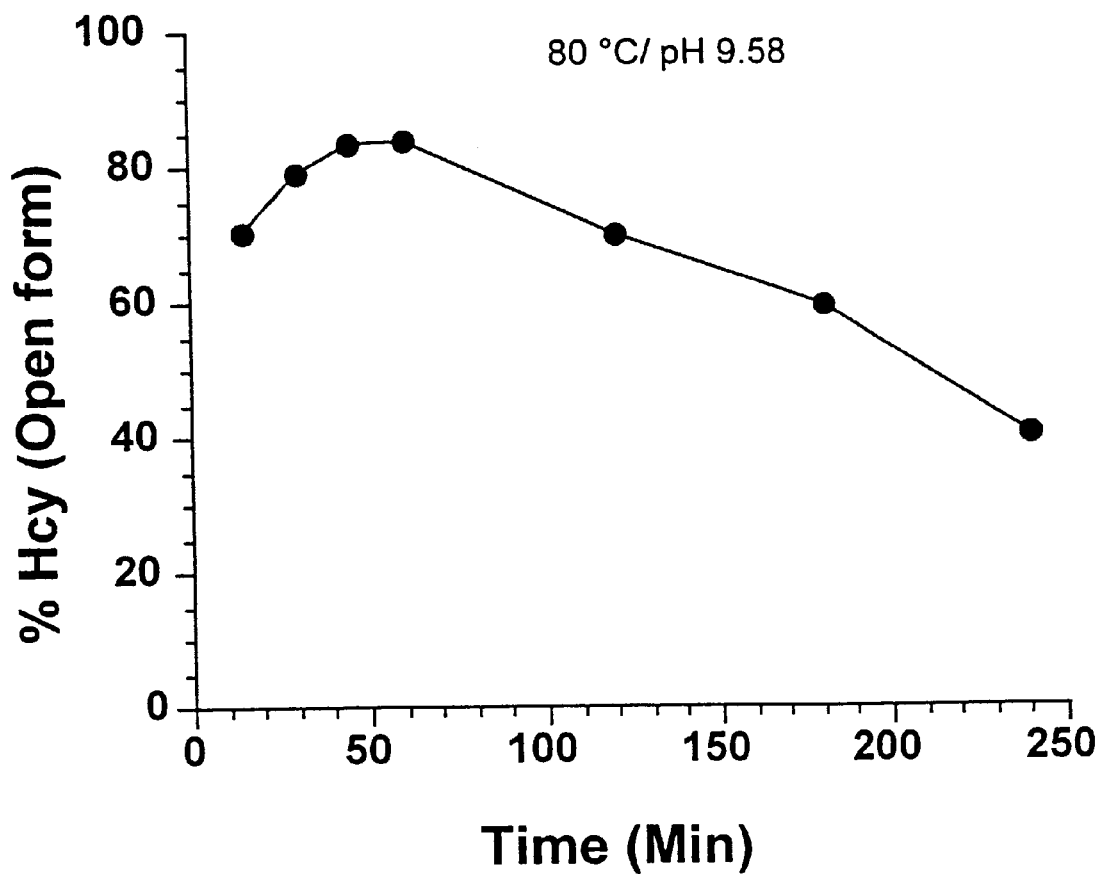
FIG. 17A shows the percent Hcy-open as a function of time. A fixed concentration of Hcy thiolactone was suspended in plasma samples precipitated with 10% TCA. The pH of the samples was increased to 6.5 with 1 M HEPES buffer (pH 8.04) and then to 9.5 with a buffer consisting of 1 M CAPS and 20 mM EDTA (pH 10.3). Samples were incubated at 80° C. for various times and thiol content was measured.
Figure 17B:
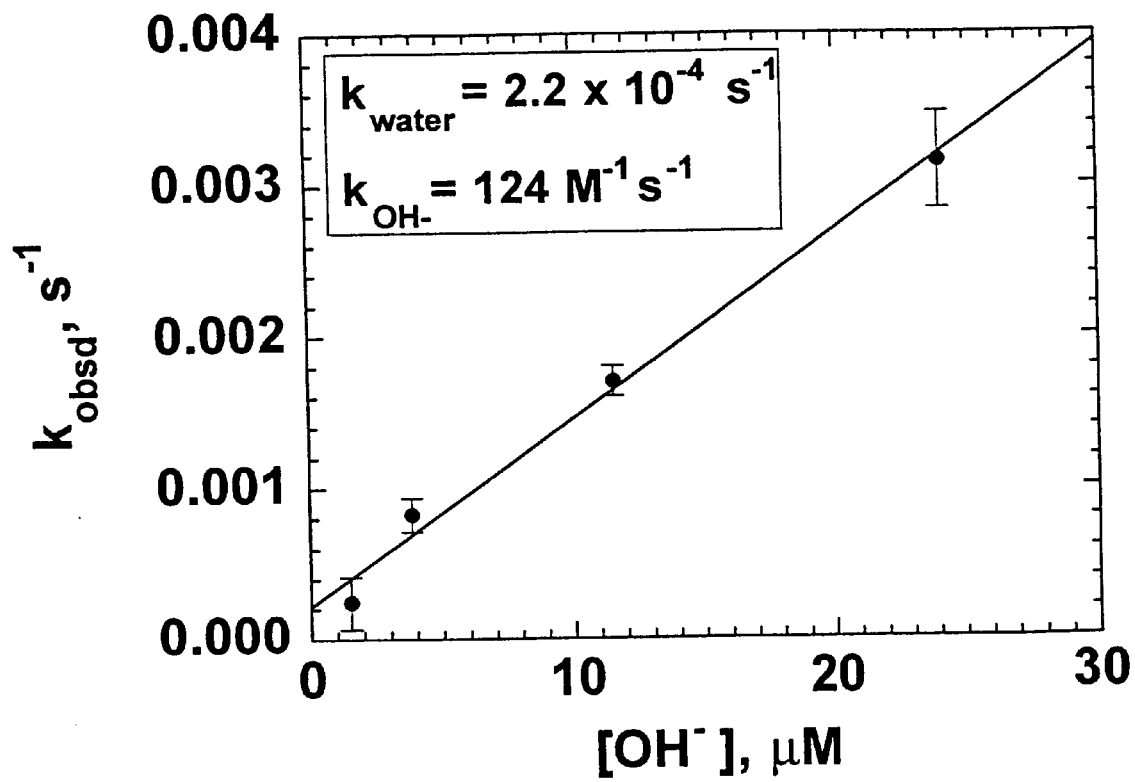
FIG. 17B shows the kinetics of ring opening of Hcy thiolactone at 80° C. as a function of hydroxide ion concentration.

The kinetics of Hcy thiolactone ring opening was measured in plasma precipitated with 10% TCA as described in Example 1 A. A fixed concentration of Hcy thiolactone was suspended in a plasma sample precipitated with 10% TCA. The pH of the plasma containing Hcy thiolactone was increased to 6.5 with 1 M HEPES buffer (pH 8.04), and 10 then to 9.5 with a buffer consisting of 1 M CAPS and 20 mM EDTA (pH 10.3). The sample was incubated at 80° C. and the thiol content was measured at various time points using Ellman's reagent. The optimum time for ring opening under these conditions was between 45–60 minutes (FIG. 17A). An increase in incubation time at high temperature gave decreased levels of detectable thiols, presumably due to the oxidation of thiols into the disulfide form. The kinetics of ring opening were further studied by suspending Hcy thiolactone at 80° C. and varying concentrations of hydroxide ion (pH>8) in 20 nM borate buffer with 200 nM NaCl (Table 1). Under these conditions, ring opening was rapid (FIG. 17B). In FIG. 17B, kObSd was determined by the equation $k_{obsd}=k_{water}+k_{OH}$.

TABLE 1

Kinetics of Hcy thiolactone opening at high pH.

| pH | $t_{1/2}$, min |
|---|---|
| 8.2 | 47 |
| 8.6 | 14 |
| 9.1 | 6.8 |
| 9.4 | 3.7 |
| 10 | (1.2) |

Example 19
Use of Tri-n-butyl Phosphine as the Reducing Agent

The reduction of plasma samples may be performed with tri-n-butyl phosphine (TBP), a non-sulfhydryl containing compound (Araki and Sako (1987) J Chromatography 422:43–52), using the following procedure: 50 µL of TBP in DMF (10% v/v) is added to 300 µL of the standard/sample in a tube, the tube is then capped and incubated for 30 minutes at 4° C.

Example 20
Determination of Optimum Ring Closure Conditions

The ring closure of Hcy at various temperatures and times was studied using the following procedure. A 500 µmol/L sample of Hcy in 0.2 M $HClO_4$ (final pH 1.0) was prepared. 300 µL aliquots of this sample were transferred to polypropylene tubes, capped and incubated at 80° C. and 100° C. for the times shown in Table 1. After the appropriate incubation time/temp, the samples were cooled to room temperature. Hcy standards were prepared in 0.2 M $HClO_4$ at concentrations of 1000, 500, 100, 50, 25, 12.5 and 0 µmol/L. HEPES buffer (86 µL) was added to the 300 µL aliquots of sample or to the standard (final pH 7.3). Ellman's reagent solution (75 µL) was added to each tube. The tubes were vortexed and 150 µL aliquots were transferred to duplicate wells of a 96 well plate and read in a spectrophotometer at 405 nm. The amount of Hcy recovered was calculated from the standard curve. The results are summarized in Table 2. Complete ring closure was achieved with incubation at 100° C. for 75 minutes (pH 1.0).

TABLE 2

% Hcy detected with Ellman's reagent solution after ring closure

| Temp | Incubation Time (min) | | | | |
|---|---|---|---|---|---|
| | 30 | 45 | 60 | 75 | 90 |
| 60° C. | 72% | 79% | 72% | 79% | 71% |
| 80° C. | 73% | 70% | 44% | 33% | 44% |
| 100° C. | 33% | 38% | 13% | 0% | 0% |

Example 21
Bead Capture Using a Filter

The following general procedure was used for bead capture of thiols in a sample. A 100 µL sample solution was added to 86 µL of HEPES buffer. 214 µL of distilled water was added, the sample was vortexed and then added to 60 mg of maleimide-conjugated beads. The tube was capped and vortexed at 200 RPM for 15 minutes and the sample was then filtered to remove the solids. 100 µL of the supernatant was removed for ring opening.

Example 22
Ring Opening of Hcy Thiolactone at Elevated temperatures

The ring opening of Hcy thiolactone at various temperatures and times was investigated. A solution of 1000 µmol/L of Hcy (SIGMA) was prepared in 0.2 M $HClO_4$. The Hcy ring closure was performed at 100° C. for 75 minutes. Remaining thiols in solution were captured on 30 mg of maleimide-conjugated cellulose beads as described in Example 21. The sample was filtered and 60 µL of CAPS buffer and 240 µL distilled water were added to 100 µL of the supernatant (final pH 10.0). The tubes were capped, vortexed and placed in a water bath at 80° C. or 100° C. for the times shown in Table 3. The samples were neutralized to pH 7.0 with 0.1 M HCl. 100 µL of Ellman's reagent solution was added to each tube, the tubes were vortexed and measured in a spectrophotometer. The results are summarized in Table 3. Maximal ring opening occurred with incubation at 80° C. for 60 minutes.

TABLE 3

| | Hcy thiolactone ring opening* | | | |
|---|---|---|---|---|
| Temp | 45 min | 60 min | 75 min | 90 min |
| 80° C. | 859 | 1322 | 1120 | 681 |
| 100° C. | 900 | 748 | 896 | 718 |

*All values are corrected OD readings

Example 23
Ring Opening of Hcy Thiolactone at Room Temperature

The conditions required to open Hcy thiolactone at room temperature were investigated (Duerre et al. (1966) Analytical Biochemistry 17:310–315). The following standards were prepared: 10,000, 5000, 2500, 1250, 625, 313, 156 and 0 µmol/L Hcy thiolactone in PBS buffer (pH 7.2). 20 µL of 1 M NaOH was added to 150 µL of these standard solutions (final pH 14.0) and the standards were incubated for 1 hour at room temperature to fully open the Hcy thiolactone. The standards were vortexed and then immediately neutralized by the addition of 20 µL 1 M HCl to each tube (final pH 7.6). The standards were vortexed, and 100 µL of Ellman's reagent solution was added to each tube. The standards were measured at 405 nm in a spectrophotometer, and a standard curve was obtained.

A solution of 5000 µmol/L Hcy thiolactone (Hcy thiolactone HCl, SIGMA) in PBS buffer was prepared and treated using the procedure described above for the standards. This sample was measured at 405 nm and the value obtained was compared to the standard curve. The results are summarized in Table 4. These results show that rapid and complete ring opening of Hcy thiolactone can be achieved at room temperature with the addition of alkali at high pH.

TABLE 4

| Ring opening at room temperature, pH 14.0 | |
|---|---|
| Initial amount of Hcy thiolactone | 5000 µmol/L |
| Amount recovered | 4486 µmol/L |
| % Recovery | 90% |

Example 24
Detection with SBDF

In addition to Ellman's reagent solution, Hcy was also detected by derivatizing with a sulfhydryl specific fluorophore, 7-fluorobenzo-2-oxa-1,3-diazole-4-sulfonate (SBDF) (Araki and Sako (1987) J. Chromatography 422:43–52), using the following procedure. 10 mg of SBDF was dissolved in 10 mL of borate buffer (pH 9.5). 100 µL of this SBDF solution was added to the sample tube. The tube was incubated at 60° C. for 60 minutes and then cooled in an ice water bath. The derivatized sample was read on a fluorometer using methods and techniques known in the art.

Example 25
Comparison of Thiol Capture on Maleimide-derivatized Cellulose or Polypropylene Beads.

A comparison of cellulose beads and polypropylene beads derivatized with maleimide was performed using Beckman AN+ standard (contains Hcy) as the standard material. Beckman AN+ standard was diluted (1:100) in PBS (pH 7.2). 300 µL aliquots of the diluted standard were prepared in polypropylene tubes for binding to maleimide-cellulose beads, maleimide-polypropylene beads or no beads. 50 µL of TBP/DMF was added to each aliquot, and the aliquots were vortexed, capped and incubated at 4° C. for 30 minutes. 250 µL of 0.6 M $HClO_4$ was added to each tube and after vortexing the solutions were filtered. 250 µL of supernatant was pipetted into a polypropylene tube, the tube was capped and incubated for 75 minutes at 100° C. The tubes were cooled to room temperature, vortexed, and 100 µL aliquots were added to 86 µL HEPES and 214 µL distilled water. The tubes were again vortexed, and then were either added to 60 mg of derivatized beads or left as a control. The tubes were vortexed at 200 RPM for 15 minutes and then filtered. 100 µL aliquots were removed, added to 60 µL CAPS and 240 µL distilled water, capped and incubated at 80–85° C. for 60 minutes. The tubes were cooled to room temperature and vortexed. 41 µL mercaptopropionylglycine and 100 µL of SBDF solution were added to all tubes, vortexed and incubated for 60 minutes at 60° C. The tubes were cooled in an ice water bath and measured by HPLC. The results are summarized in Table 5.

TABLE 5

Comparison of polypropylene and cellulose beads

|  | Recovered | % Recovered |
|---|---|---|
| Control Sample (no bead) | 50 μmol/L |  |
| Cellulose Bead | 25 μmol/L | 50% (relative to control) |
| Polypropylene Bead | 31.5 μmol/L | 63% (relative to control) |

Example 26
Using Serum Sample and HPLC Analysis for Detection of Hcy

In this experiment, a serum sample containing 35 μmol/L of Hcy (as determined by HPLC) was used. 300 μL aliquots were prepared in polypropylene tubes for binding to maleimide-cellulose beads, maleimide-polypropylene beads or no beads. 50 μL of TBP/DMF was added to each aliquot, the aliquots were vortexed, capped and incubated at 4° C. for 30 minutes. 250 μL of HClO$_4$ was added to each tube, and after vortexing the aliquots were filtered. 250 μL of the supernatant was pipetted into polypropylene tube and incubated 75 minutes at 100° C. The tubes were cooled to room temp, vortexed and 100 μL to 86 μL HEPES and 214 μL distilled water was added. The aliquots were vortexed and added to 60 mg beads or left as controls. After vortexing at 200 RPM for 15 minutes, the aliquots were filtered. 100 μL aliquots were added to 60 μL CAPS and 240 μL distilled water, vortexed capped and incubated at 80–85° C. for 60 minutes. The tubes were cooled to room temperature and vortexed. 41 μL mercaptopropionyl-glycine and 100 μL of SBDF solution were added to all tubes, vortexed and incubated for 60 minutes at 60° C. The tubes were cooled in an ice water bath and measured by HPLC. The results are summarized in Table 6.

TABLE 6

HPLC analysis of serum sample

|  | Recovered | % Recovered |
|---|---|---|
| Control Sample (no bead) | 37 μmol/L |  |
| Cellulose Bead | 9 μmol/L | 24% (relative to control) |
| Polypropylene Bead | 9 μmol/L | 22% (relative to control) |

Example 27
Modified Full Procedure

The following procedure summarizes the procedures described in examples 19–26. Beckman AN+ standard (containing Hcy) was diluted in PBS (pH 7.2) to construct a standard curve between 0 and 100 μmol/L. 300 μL aliquots of standard or sample were prepared in polypropylene tubes. 50 μL of TBP/DMF was added to each aliquot, and the aliquots were vortexed, capped and incubated at 4° C. for 30 minutes. 250 μL of 0.6 M HClO$_4$ was added to each tube, and after vortexing the solutions were filtered. 250 μL of supernatant was pipetted into a polypropylene tube, the tube was capped and incubated for 75 minutes at 100° C. The tubes were cooled to room temperature, vortexed, and 100 μL aliquots were added to 86 μL HEPES and 214 μL distilled water. The tubes were again vortexed, and then were added to 60 mg of beads (final pH 7.3). The tubes were vortexed at 200 RPM for 15 minutes and filtered. 100 μL aliquots were removed, added to 60 μL CAPS and 240 μL distilled water, capped and incubated at 80–85° C. for 60 minutes. The tubes were then cooled to room temperature, vortexed, and 100 μL of SBDF solution was added. After incubating for 60 minutes at 60° C., the tubes were cooled in an ice water bath and then duplicate aliquots were placed into a 96 well plate. The aliquots were read on a fluorometer.

We claim:

1. A method for detecting the presence of homocysteine in a sample that may contain homocysteine, comprising the steps of (a) converting homocysteine in the sample to homocysteine thiolactone; (b) reacting free thiol-containing compounds in the sample with a thiol-capturing agent; (c) reconverting the homocysteine thiolactone to homocysteine; and (d) detecting the presence of homocysteine in the sample.

2. The method of claim 1 wherein homocysteine is converted to homocysteine thiolactone by adjusting the pH of the sample to between pH 0–5.

3. The method of claim 1 wherein said thiol-capturing agent is an α,β-unsaturated compound.

4. The method of claim 3 wherein the thiol-capturing agent is maleimide or vinyl sulfone.

5. The method of claim 1 wherein said thiol-capturing agent is a haloacetate.

6. The method of claim 5 wherein said haloacetate is iodoacetate.

7. The method of claim 1 wherein the thiol-capturing agent is coupled to a solid support.

8. The method of claim 7 wherein said solid support is selected from the group consisting of controlled pore glass, cellulose, polypropylene beads, polystyrene beads and polyethylene glycol.

9. The method of claim 7 wherein after step (b), the products of the reaction between the thiol-containing compounds and the thiol-capturing agent are removed from the sample.

10. The method of claim 1 which is a homogeneous method.

11. The method of claim 1 wherein after step (b) any unreacted thiol-capturing agent is quenched by the addition of a quenching reagent.

12. The method of claim 11 wherein the quenching reagent is selected from the group consisting of dienes, reducing agents and halogens.

13. The method of claim 1 wherein in step (c), the homocysteine thiolactone is reconverted to homocysteine by adjusting the pH of between 7–12.

14. The method of claim 1 wherein said detection of said homocysteine is a photometric method.

15. The method of claim 14 wherein said photometric method comprises treating the homocysteine from step (d) with Ellman's reagent or 7-fluorobenzo-2-oxa-1,3-diazole-4-sulfonate (SBDF).

16. The method of claim 1 wherein said sample is a biological sample.

17. The method of claim 16 wherein the biological sample is a biological tissue or a biological fluid.

18. The method of claim 17 wherein said biological fluid is selected from the group consisting of urine, blood, plasma, serum, saliva, semen, stool, sputum, cerebral spinal fluid, tears, mucus and amniotic fluid.

19. The method of claim 17 wherein said biological tissue is selected from the group consisting of connective tissue, epithelium, muscle tissue, nerve tissue, organs, tumors, lymph nodes, arteries, and cells.

20. The method of claim 1, further comprising, before step (a), combining the sample with a releasing reagent which reduces the disulfide forms of thiol-containing compounds.

21. The method of claim 20 wherein said releasing reagent is selected from the group consisting of dithiothreitol, dithioerythritol, 2-mercaptoethanol, thioglycolic acid, glutathione, tributylphosphine, tris(2-carboxyethyl)phosphine, sodium cyanoborohydride, sodium borohydride, potassium borohydride and free metals.

22. A method for determining the quantity of homocysteine in a sample that may contain homocysteine, comprising the steps of (a) converting homocysteine in the sample to homocysteine thiolactone; (b) reacting free thiol-containing compounds in the sample with a thiol-capturing agent; (c) reconverting the homocysteine thiolactone to homocysteine; and (d) determining the quantity of homocysteine in the sample.

23. The method of claim 22 wherein homocysteine is converted to homocysteine thiolactone by adjusting the pH of the sample to between pH 0–5.

24. The method of claim 22 wherein said thiol-capturing agent is an $\alpha,\beta$-unsaturated compound.

25. The method of claim 24 wherein the thiol-capturing agent is maleimide or vinyl sulfone.

26. The method of claim 22 wherein said thiol-capturing agent is a haloacetate.

27. The method of claim 26 wherein said haloacetate is iodoacetate.

28. The method of claim 22 wherein the thiol-capturing agent is coupled to a solid support.

29. The method of claim 28 wherein said solid support is selected from the group consisting of controlled pore glass, cellulose, polypropylene beads, polystyrene beads and polyethylene glycol.

30. The method of claim 28 wherein after step (b), the products of the reaction between the thiol-containing compounds and the thiol-capturing agent are removed from the sample.

31. The method of claim 22 which is a homogeneous method.

32. The method of claim 22 wherein after step (b) any unreacted thiol-capturing agent is quenched by the addition of a quenching reagent.

33. The method of claim 32 wherein the quenching reagent is selected from the group consisting of dienes, reducing agents and halogens.

34. The method of claim 22 wherein in step (c), the homocysteine thiolactone is reconverted to homocysteine by adjusting the pH of between 7–12.

35. The method of claim 22 wherein said detection of said homocysteine is a photometric method.

36. The method of claim 35 wherein said photometric method comprises treating the homocysteine from step (d) with Ellman's reagent or SBDF.

37. The method of claim 22 wherein said sample is a biological sample.

38. The method of claim 37 wherein the biological sample is a biological tissue or a biological fluid.

39. The method of claim 38 wherein said biological fluid is selected from the group consisting of urine, blood, plasma, serum, saliva, semen, stool, sputum, cerebral spinal fluid, tears, mucus and amniotic fluid.

40. The method of claim 38 wherein said biological tissue is selected from the group consisting of connective tissue, epithelium, muscle tissue, nerve tissue, organs, tumors, lymph nodes, arteries, and cells.

41. The method of claim 22, further comprising, before step (a), combining the sample with a releasing reagent which reduces disulfide forms of thiol-containing compounds.

42. The method of claim 41 wherein said releasing reagent is selected from the group consisting of dithiothreitol, dithioerythritol, 2-mercaptoethanol, thioglycolic acid, glutathione, tributylphosphine, tris(2-carboxyethyl)phosphine, sodium cyanoborohydride, sodium borohydride, potassium borohydride and free metals.

43. A method of detecting the presence of homocysteine in a sample that may contain homocysteine, comprising the steps of (a) converting homocysteine to homocysteine thiolactone; (b) reacting free thiol-containing compounds in the sample with a thiol-capturing agent; and (c) detecting the presence of the homocysteine thiolactone in the sample.

44. The method of claim 43 wherein homocysteine is converted to homocysteine thiolactone by adjusting the pH of the sample to pH 0–5.

45. The method of claim 43 wherein said thiol-capturing agent is an a,p- unsaturated compound.

46. The method of claim 45 wherein the thiol-capturing agent is maleimide or vinyl sulfone.

47. The method of claim 43 wherein said thiol-capturing agent is a haloacetate.

48. The method of claim 47 wherein said haloacetate is iodoacetate.

49. The method of claim 43 wherein said detection of said homocysteine thiolactone is a photometric method.

50. The method of claim 43 wherein said sample is a biological sample.

51. The method of claim 50 wherein the biological sample is a biological tissue or a biological fluid.

52. The method of claim 51 wherein said biological fluid is selected from the group consisting of urine, blood, plasma, serum, saliva, semen, stool, sputum, cerebral spinal fluid, tears, mucus and amniotic fluid.

53. The method of claim 51 wherein said biological tissue is selected from the group consisting of connective tissue, epithelium, muscle tissue, nerve tissue, organs, tumors, lymph nodes, arteries, and cells.

54. The method of claim 43, further comprising, before step (a), combining the sample with a releasing reagent which reduces all disulfide forms of thiol-containing compounds.

55. The method of claim 54, wherein said reducing reagent is selected from the group consisting of dithiothreitol, dithioerythritol, 2-mercaptoethanol, thioglycolic acid, glutathione, tri-n-butylphosphine, tris(2-carboxyethyl)phosphine, sodium cyanoborohydride, sodium borohydride, potassium borohydride and free metals.

56. A method for detecting the presence of homocysteine in a sample that may contain homocysteine, comprising the steps of (a) converting homocysteine in the sample to homocysteine thiolactone; (b) reacting free thiol-containing compounds in the sample with a thiol-capturing agent; (c) reacting the homocysteine thiolactone with a nucleophile; and (d) detecting the presence of the homocysteine in the sample.

57. The method of claim 56 wherein said nucleophile is an amine.

58. A method for determining the quantity of homocysteine in a sample that may contain homocysteine, comprising the steps of (a) converting homocysteine in the sample to homocysteine thiolactone; (b) reacting free thiol-containing compounds in the sample with a thiol-capturing agent; (c) reacting the homocysteine thiolactone with a nucleophile; and (d) determining the quantity of the homocysteine in the sample.

59. The method of claim 58 wherein said nucleophile is an amine.

60. A kit for detecting the presence and/or quantity of Hcy comprising: a means for converting homocysteine to homocysteine thiolactone, a thiol-capturing agent, a means for reconverting Hcy thiolactone to Hcy, and a means for detecting the presence and/or quantity of Hcy in the sample.

61. The kit as described in claim 60, further comprising a releasing agent which reduces disulfide forms of thiol-containing compounds.

* * * * *

UNITED STATES PATENT AND TRADEMARK OFFICE
CERTIFICATE OF CORRECTION

PATENT NO. : 6,020,206
DATED : February 1, 2000
INVENTOR(S) : Chandra Vargeese, et al.

It is certified that error appears in the above-identified patent and that said Letters Patent is hereby corrected as shown below:

Column 5, line 32, after "time" insert --for--.

Column 6, line 22, change "HC1O4" to --HC1O$_4$--.

Signed and Sealed this

Thirteenth Day of June, 2000

Attest:

Q. TODD DICKINSON

Attesting Officer        Director of Patents and Trademarks